United States Patent [19]

Setoi et al.

[11] Patent Number: 4,929,639

[45] Date of Patent: May 29, 1990

[54] OXYGEN-CONTAINING HETEROCYCLIC COMPOUND

[75] Inventors: Hiroyuki Setoi; Akio Kuroda; Hirokazu Tanaka; Hideo Hirai; Hiroshi Marusawa; Masashi Hashimoto, all of Tsukuba, Japan

[73] Assignee: Fujisawa Pharmaceutical Company, Ltd., Osaka, Japan

[21] Appl. No.: 208,665

[22] Filed: Jun. 20, 1988

[51] Int. Cl.$^5$ .................. A61K 31/335; C07D 319/06
[52] U.S. Cl. ...................................... 514/452; 549/373
[58] Field of Search ................. 549/373, 426; 514/452

[56] References Cited

U.S. PATENT DOCUMENTS 4,567,197  1/1986  Brewster et al. .................. 549/373

FOREIGN PATENT DOCUMENTS 2451374 10/1980 France .

Primary Examiner—Nicky Chan
Attorney, Agent, or Firm—Oblon, Spivak, McClelland, Maier & Neustadt

[57] ABSTRACT

The invention relates to treatment of diseases caused by thromboxane $A_2$ comprising administering a compound

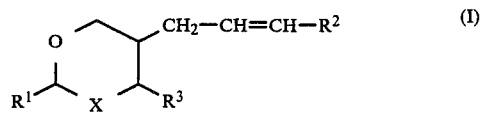

wherein
 $R^1$ is hydrogen or lower alkyl,
 $R^2$ is carboxy(lower)alkyl or protected carboxy(lower)alkyl and
 $R^3$ is —CH=N—$R^4$ in which $R^4$ is arylureido or arylthioureido and
 X is —O—, or a pharmaceutically acceptable salt thereof.

9 Claims, No Drawings

OXYGEN-CONTAINING HETEROCYCLIC COMPOUND

This invention relates to a new oxygen-containing heterocyclic compound and pharmaceutically acceptable salts thereof.

More particularly, it relates to a new oxygen-containing heterocyclic compound and pharmaceutically acceptable salt thereof which are thromboxane $A_2$ ($TXA_2$) antagonists and therefore useful as therapeutical agents for diseases caused by $TXA_2$ (e.g. thrombosis, asthma, etc.).

The oxygen-containing heterocyclic compound of this invention can be represented by the following formula:

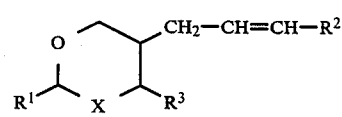
(I)

wherein
$R^1$ is hydrogen or lower alkyl,
$R^2$ is carboxy(lower)alkyl or protected carboxy(lower)alkyl,
$R^3$ is —$CH_2NH$—$R^4$, —$CH$=$N$—$R^4$ or —$CH_2$—$R^5$
in which
$R^4$ is acyl, acylamino, heterocyclic amino, heterocyclic(lower)alkyl or ar(lower)alkoxy and
$R^5$ is acyloxy or heterocyclic(lower)alkoxy and
X is —O— or —$CH_2$—.

Suitable pharmaceutically acceptable salts of the object compound (I) are conventional non-toxic salts and may include a metal salt such as an alkali metal salt (e.g., sodium salt, potassium salt, etc.) and an alkaline earth metal salt (e.g., calcium salt, magnesium salt, etc.), ammonium salt, an organic amine salt (e.g., trimethylamine salt, triethylamine salt, pyridine salt, picoline salt, dicyclohexylamine salt, N,N'-dibenzylethylenediamine salt, etc.), an organic acid salt (e.g., acetate, maleate, tartrate, methanesulfonate, benzenesulfonate, toluenesulfonate, etc.), an inorganic acid salt (e.g., hydrochloride, hydrobromide, sulfate, phosphate, etc.), or a salt with an amino acid (e.g., arginine, aspartic acid, glutamic acid, etc.), and the like.

According to this invention, the new heterocyclic compound (I) and pharmaceutically acceptable salt thereof can be prepared by, for example, the following processes.

Process 1:

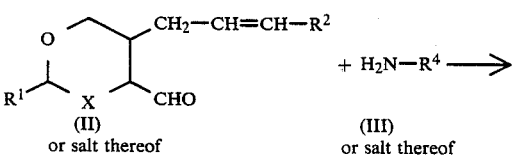

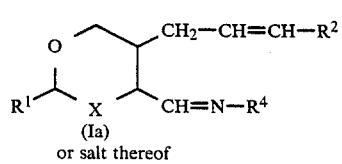

Process 2:

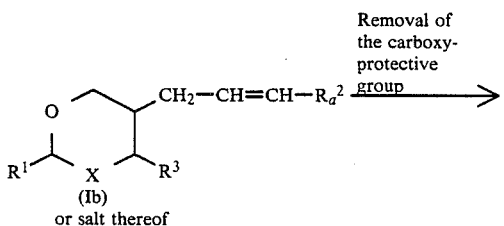

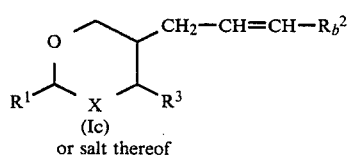

Process 3:

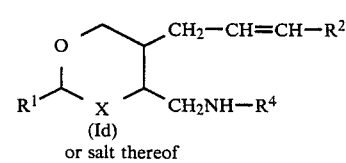

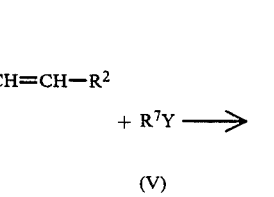

Process 4:

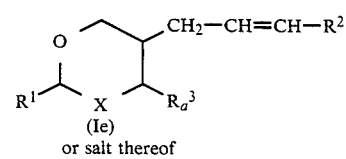

Process 5:

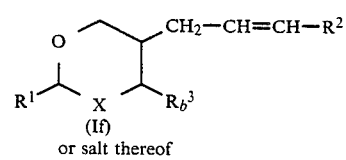

wherein
$R^1$, $R^2$, $R^3$, $R^4$ and X are each as defined above,
$R_a^2$ is a protected carboxy(lower)alkyl,
$R_b^2$ is carboxy(lower)alkyl, $R_a^3$ is ar(lower)alkoxyiminomethyl or heterocyclic(lower)alkoxymethyl, $R_b^3$ is acyloxymethyl or acylaminomethyl, $R^6$ is hydroxyiminomethyl or hydroxymethyl, $R^7$ is ar(lower)alkyl or heterocyclic(lower)alkyl, $R^8$ is hydroxymethyl or aminomethyl and Y is acid residue.

The starting compounds (II), (IV) and (VI) are new compounds and can be prepared, for example by the following preparations and similar manner thereto.

Preparation A

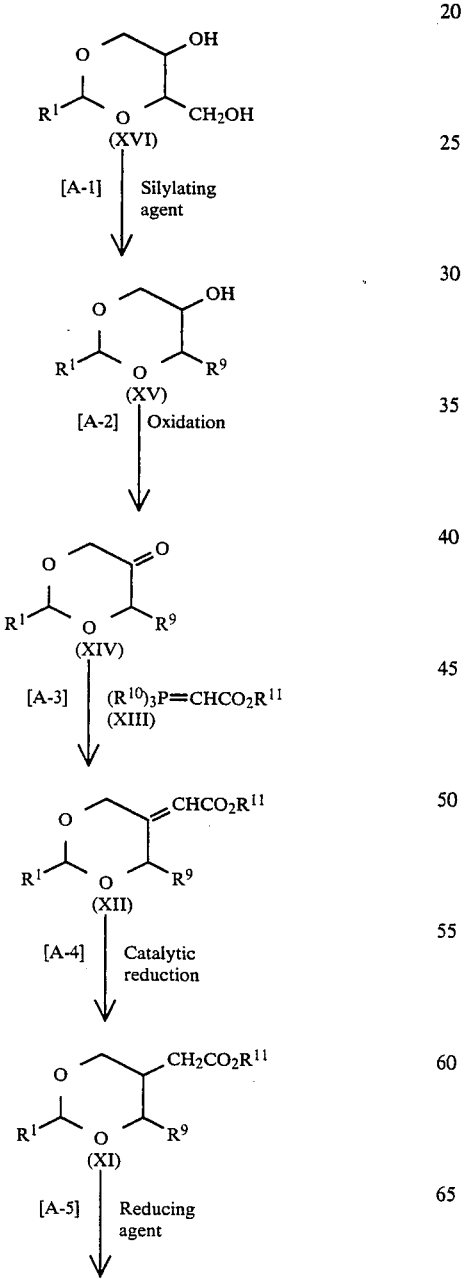

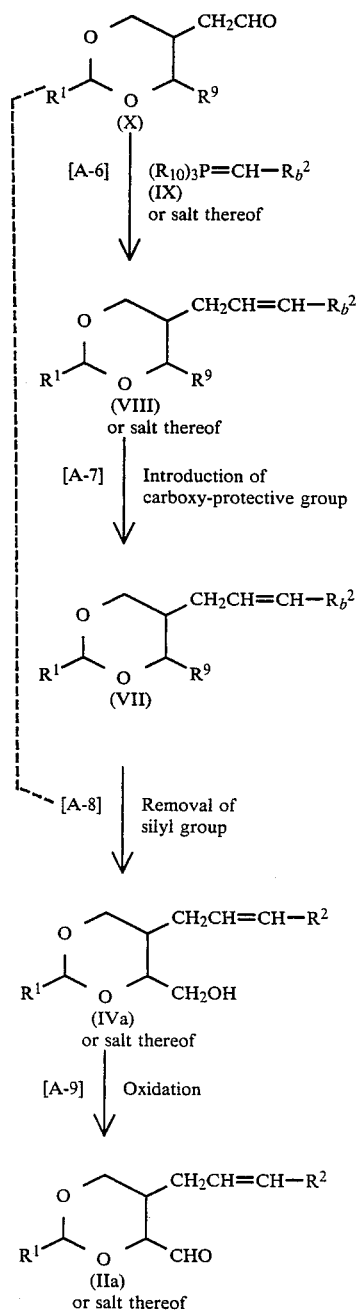

Preparation B

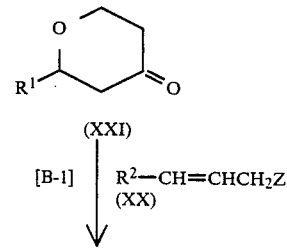

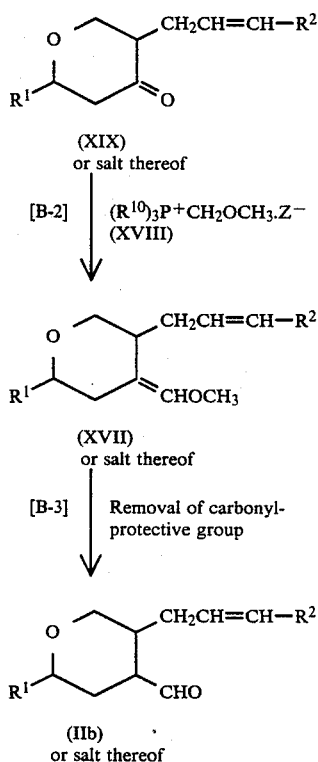

(XIX) or salt thereof

[B-2]　(R$^{10}$)$_3$P$^+$CH$_2$OCH$_3$.Z$^-$ (XVIII)

(XVII) or salt thereof

[B-3]　Removal of carbonyl-protective group (IIb) or salt thereof

Preparation C

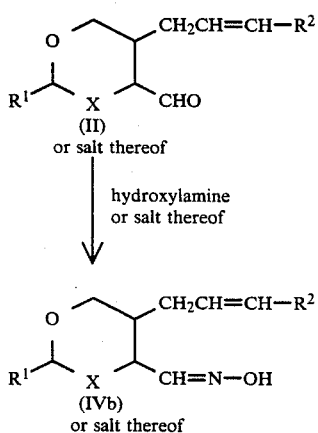

(II) or salt thereof hydroxylamine or salt thereof (IVb) or salt thereof

Preparation D

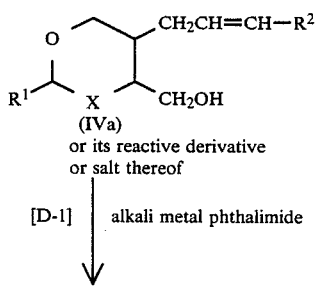

(IVa) or its reactive derivative or salt thereof

[D-1]　alkali metal phthalimide

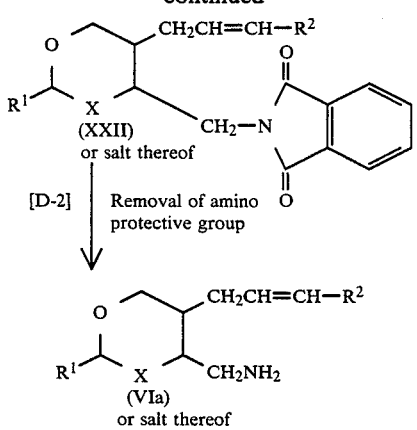

(XXII) or salt thereof

[D-2]　Removal of amino protective group (VIa) or salt thereof wherein
R$^1$, R$^2$, R$_a^2$, R$_b^2$ and X are each defined above,
R$^9$ is a silylated hydroxymethyl,
R$^{10}$ is aryl,
R$^{11}$ is lower alkyl, and
Z is acid residue.

The salts of the compounds (Ia), (Ib), (Ic), (Id), (Ie), (If), (VI) and (VIa) are the same as those exemplified in the explanation of pharmaceutically acceptable salts of the compound (I).

The salts of the compounds (II), (IIa), (IIb), (IV), (IVa), (IVb), (VIII), (IX), (XVII), (XVIII) and (XXI) are the same base salt as those exemplified in the explanation of the compound (I).

The salts of the compound (III) are the same acid salt as those exemplified in the explanation of the compound (I).

In the above and subsequent descriptions of this specification, suitable examples and illustrations of the various definitions are explained in detail in the followings.

The term "lower" is intended to mean 1 to 6 carbon atom(s), unless otherwise indicated.

Suitable "lower alkyl" in the terms "lower alkyl", "carboxy(lower)alkyl", "protected carboxy(lower)alkyl" and "heterocyclic(lower)alkyl" may include methyl, ethyl, propyl, isopropyl, butyl, isobutyl, t-butyl, pentyl hexyl and the like.

Suitable "acyl" in the terms "acyl", "acylamino", "acyloxy", "acyloxymethyl" and "acylaminomethyl" may include arylcarbamoyl (e.g. phenylcarbamoyl, tolylcarbamoyl, xylylcarbamoyl, naphthylcarbamoyl, etc.), arylthiocarbamoyl (e.g. phenylthiocarbamoyl, tolylthiocarbamoyl, xylylthiocarbamoyl, naphthylthiocarbamoyl, etc.), lower alkoxycarbonyl (e.g. methoxycarbonyl, ethoxycarbonyl, propoxycarbonyl, isopropoxycarbonyl, butoxycarbonyl, isobutoxycarbonyl, t-butoxycarbonyl, pentyloxycarbonyl, hexyloxycarbonyl, etc.), ar(lower)alkylcarbamoyl such as phenyl(-lower)alkylcarbamoyl (e.g. benzylcarbamoyl, etc.), ar(-lower)alkylglyoxyloyl such as phenyl(lower)alkylglyoxyloyl (e.g. benzylglyoxyloyl, etc.), heterocyclic carbonyl such as 5-membered S-containing heteromonocyclic carbonyl (e.g. thienylcarbonyl, etc.), and the like.

Suitable "aryl" may include phenyl, tolyl, xylyl, napthyl and the like.

Suitable "ar(lower)alkoxy" in the terms "ar(lower)alkoxy" and "ar(lower)alkoxyiminomethyl" may include mono(or di or tri)phenyl(lower)alkoxy (e.g. benzylmethoxy, diphenylmethoxy, etc.) and the like.

Suitable "protected carboxy" in the term "protected carboxy (lower) alkyl" may include lower alkoxycarbonyl (e.g. methoxycarbonyl, ethoxycarbonyl, propoxycarbonyl, etc.) and the like.

Suitable "heterocyclic amino" may include 6-membered N-containing heteromonocyclic amino (e.g. pyridylamino, etc.), benzene-fused 6-membered N-containing heteromonocyclic amino (e.g phthalazinylamino, etc.) and the like.

Suitable "heterocyclic" in the terms "heterocyclic(lower)alkyl", "heterocyclic(lower)alkoxy" and "heterocyclic(lower)alkoxymethyl" may include 6-membered N-containing heteromonocyclic (e.g. pyridyl, etc.) and the like.

Suitable "lower alkoxy" in the terms "heterocyclic(lower)alkoxy" and "heterocyclic(lower)alkoxymethyl" may include methoxy, ethoxy, propoxy and the like.

Suitable "acid residue" may include halogen (e.g. fluorine, chlorine, bromine, iodine, etc.) and the like.

The term "silylated hydroxymethyl" is a hydroxymethyl silylated by a conventional silylating agent such as tri(lower)alkylhalosilane (e.g, t-butyldimethylchlorosilane) and suitable "silylated hydroxymethyl" may include tri(lower)alkylsiloxymethyl (e.g. t-butyldimethylsiloxymethyl, etc.) and the like.

Preferable embodiment of the object compound (I) are as follows.

Preferable embodiment of $R^1$ is hydrogen or lower alkyl; $R^2$ is carboxy(lower)alkyl or protected carboxy(lower)alkyl; $R^3$ is —$CH_2NH$—$R^4$, —$CH=N$—$R^4$ or —$CH_2$—$R^5$ in which $R^4$ is acyl [more preferably arylcarbamoyl[most preferably phenylcarbamoyl], ar(lower)alkylcarbamoyl], ar(lower)alkylglyoxyloyl, [most preferably phenyl(lower)alkylglyoxyloyl], ar(lower)alkylglyoxyloyl [most preferably phenyl(lower)alkylglyoxyloyl]], acylamino [more preferably arylureido [most preferably phenylureido], arylthioureido [most preferably phenylthioureido], lower alkoxycarbonylamino or heterocyclic carbonylamino [more preferably 5-membered S-containing heteromonocyclic carbonylamino [most preferably thienylcarbonylamino]], heterocyclic amino [more preferably 6-membered N-containing heteromonocyclic amino [most preferably pyridylamino] or benzene-fused 6-membered N-containing heteromonocyclic amino [most preferably phthalazinylamino]], heterocyclic(lower)alkyl [more preferably 6-membered N-containing heteromonocyclic(lower)alkyl [most preferably pyridyl(lower)alkyl]], or ar(lower)alkoxy [more preferably mono(or di or tri)phenyl(lower)alkoxy [most preferably diphenyl(lower)alkoxy]]; $R^5$ is acyloxy [more preferably arylcarbamoyloxy [most preferably phenylcarbamoyloxy]] or heterocyclic(lower)alkoxy[more preferably 6-membered N-containing heteromonocyclic(lower)alkoxy [most preferably pyridyl(lower)alkoxy]]; and X is —O— or —$CH_2$—.

The processes and preparations as illustrated above are explained in more detail in the followings.

Process 1

The object compound (Ia) or salt thereof can be prepared by reacting the compound (II) or salt thereof with the compound (III) or salt thereof.

This reaction is usually carried out in a solvent which does not adversely influence the reaction such as water, methanol, ethanol, propanol, N,N-dimethylformamide, tetrahydrofuran, dioxane, dimethylsulfoxide and the like.

The reaction may preferably be carried out in the presence of a small quantity of inorganic or organic acid such as hydrochloric acid, acetic acid, trifluoroacetic acid and the like.

The reaction temperature is not critical and the reaction can be carried out under cooling to under heating.

Process 2

The object compound (Ic) or salt thereof can be prepared by subjecting the compound (Ib) or salt thereof to removal reaction of the carboxy-protective group.

The removal reaction of this process include hydrolysis and the like.

The reaction is usually carried out in a solvent which does not adversely influence the reaction such as water, methanol, ethanol, propanol and the like.

The reaction can preferably be conducted in the presence of an organic or inorganic base such as alkali metal (e.g. sodium), alkaline earth metal (e.g. calcium), alkali or alkaline earth metal hydride (e g. sodium hydride, calcium hydride, etc.), alkali or alkaline earth metal hydroxide (e.g. sodium hydroxide, potassium hydroxide, calcium hydroxide, etc.), alkali or alkaline earth metal carbonate or bicarbonate (e.g. sodium carbonate, potassium carbonate, sodium bicarbonate), alkali or alkaline earth metal alkoxide (e.g. sodium ethoxide, lithium methoxide, magnesium methoxide), trialkylamine (e.g. triethylamine), pyridine, bicyclodiaza compound (e.g. 1,5-diazabicyclo[3,4,0]nonene-5, 1,5-diazabicyclo[5,4,0]undecene-5, etc.) and the like.

The reaction temperature is not critical and the reaction can be carried out under cooling to under heating.

Process 3

The object compound (Id) or salt thereof can be prepared by reducing the compound (Ia) or salt thereof.

The reduction is usually carried out by using a reducing agent such as alkali metal borohydride (e.g. sodium borohydride, etc.), alkali metal cyanoborohydride (e.g. sodium cyanoborohydride, etc.) and the like.

The reduction is usually carried out in a solvent which does not adversely influence the reaction such as methanol, ethanol, acetic acid, tetrahydrofuran, N,N-dimethylformamide, dimethylsulfoxide, dioxane and the like.

The reaction temperature is not critical and the reaction can be carried out under cooling to under heating.

Process 4

The object compound (Ie) or salt thereof can be prepared by reacting the compound (IV) or salt thereof with the compound (V).

The reaction is usually carried out in a solvent which does not adversely influence the reaction such as N,N-dimethylformamide, tetrahydrofuran, dimethylsulfoxide, dioxane and the like.

The reaction can preferably be carried out in presence of inorganic or organic base as those exemplified in the explanation of the above Process 2.

The reaction temperature is not critical and the reaction can be carried out under cooling to under heating.

Process 5

The object compound (If) or salt thereof can be prepared by reacting the compound (VI) or salt thereof with an acylating agent.

The acylating agent may include an organic acid (i.e. $R^{12}OH$ in which $R^{12}$ is acyl) or its reactive derivative.

The suitable reactive derivative of the organic acid may be a conventional one such as an acid halide (e.g. acid chloride, acid bromide, etc.), an acid azide, an acid anhydride, an activated amide, an activated ester, an isocyanate [e.g. aryl isocyanate(e.g. phenyl isocyanate, etc.), ar(lower)alkyl isocyanate (e.g. phenyl(lower)alkyl isocyanate, etc.), etc.].

When free acid is used as an acylating agent, the acylation reaction may preferably be conducted in the presence of a conventional condensing agent such as N,N'-dicyclohexylcarbodiimide and the like.

The reaction can preferably be conducted in the presence of an inorganic or organic base as those exemplified in the explanation of the above Process 2.

This reaction is usually carried out in a solvent which does not adversely influence the reaction such as methanol, ethanol, propanol, tetrahydrofuran, chloroform and the like.

The reaction temperature is not critical and the reaction can be carried out under cooling to under heating.

Preparation A-1

The compound (XV) can be prepared by reacting the compound (XVI) with a silylating agent.

Among the starting compound (XVI), (2R,4S,5R)-5-hydroxy-4-hydroxymethyl-2-methyl-1,3-dioxane (2,4-D-ethylidene-D-erythritol) and preparation thereof were described in Journal of the American Chemical Society 82, 2302 (1960) and other compounds (XVI) can be prepared in a similar manner thereto.

The silylating agent includes a conventional silylating agent (e.g. trialkylhalosilane, etc.).

This reaction is usually carried out in a solvent which does not adversely influence the reaction (e.g. N,N-dimethylformamide, etc.) under cooling to heating in a conventional manner.

Preparation A-2

The compound (XIV) can be prepared by oxidizing the compound (XV).

The oxidation is carried out by using a conventional oxidizing agent (e.g. dimethylsulfoxide, etc.) in a solvent which does not adversely influence the reaction (e.g. benzene, etc.) under cooling to heating in a conventional manner.

Preparation A-3

The compound (XII) can be prepared by reacting the compound (XIV) with the compound (XIII).

The reaction is usually carried out in a solvent which does not adversely influence the reaction (e.g. tetrahydrofuran, etc.) under cooling to under heating in a conventional manner.

Preparation A-4

The compound (XI) can be prepared by subjecting the compound (XII) to the catalytic reduction.

The catalytic reduction is carried out in a solvent which does not adversely influence the reaction (e.g. ethanol) around at room temperature in a conventional manner.

Preparation A-5

The compound (X) can be prepared by reducing the compound (XI).

The reduction is usually carried out by using a reducing agent (e.g. alkyl aluminum hydride, etc.) in a solvent which does not adversely in the reaction (e.g. toluene, etc.) at room temperature to under cooling in a conventional manner.

Preparation A-6

The compound (VIII) or salt thereof can be prepared by reacting the compound (X) with the compound (IX) or salt thereof.

The reaction is usually carried out in a solvent which does not adversely influence the reaction (e.g. dimethylsulfoxide, etc.) under cooling to heating in a conventional manner.

Preparation A-7

The compound (VII) can be prepared by subjecting the compound (VIII) or salt thereof to introduction reaction of carboxy-protective group.

The reaction is usually carried out in a solvent which does not influence the reaction (e.g. N,N-dimethylformamide, etc.) under cooling to under heating in a conventional manner.

Preparation A-8

The compound (IVa) or salt thereof can be prepared by subjecting the compound (VIII) or salt thereof or the compound (VII) to removal reaction of the silyl group.

The reaction is carried out in a solvent which does not adversely influence the reaction (e.g. tetrahydrofuran, etc.) under cooling to heating in a conventional manner.

Preparation A-9

The compound (IIa) or salt thereof can be prepared by oxidizing the compound (IVa) or salt thereof.

The oxidation is carried out by using a conventional oxidizing agent capable of converting the hydroxymethyl group into the formyl group (e.g. chromium trioxide, etc.)

The reaction is usually carried out in a solvent which does not adversely influence the reaction (e.g. dichloromethane, etc.) under cooling to under heating.

Preparation B-1

The compound (XIX) or salt thereof can be prepared by reacting the compound (XXI) with the compound (XX).

The reaction is usually carried out in a solvent which does not adversely influence the reaction (e.g. tetrahydrofuran, etc.) under cooling in a conventional manner.

Preparation B-2

The compound (XVII) can be prepared by reacting the compound (XIX) or salt thereof with the compound (XVIII).

The reaction is usually carried out in a solvent which does not adversely influence the reaction (e.g. dimethylsulfoxide, etc.) under cooling to under heating in a conventional manner.

Preparation B-3

The compound (IIb) or salt thereof can be prepared by subjecting the compound (XVII) or salt thereof to removal reaction of the carbonyl-protective group.

The reaction is usually carried out in a solvent which does not adversely influence the reaction (e.g. methanol, etc.) under cooling to under heating in a conventional manner.

Preparation C

The compound (IVb) or salt thereof can be prepared by reacting the compound (II) or salt thereof with hydroxylamine or salt thereof.

The reaction is usually carried out in a solvent which does not adversely influence the reaction (e.g. water, methanol, etc.) under cooling to under heating in a conventional manner.

Preparation D-1

The compound (XXII) or salt thereof can be prepared by the compound (IVa) or its reactive derivative or salt thereof with alkali metal phthalimide.

The reaction is usually carried out in a solvent which does not adversely influence the reaction (e.g. pyridine, etc.) under cooling to under heating in a conventional manner.

Preparation D-2

The compound (VIa) or salt thereof can be prepared by subjecting the compound (XXII) or salt thereof to removal reaction of the amino-protective group.

The reaction is usually carried out by using a conventional removal agent of the amino-protective group (e.g. hydrazine, etc.) in a solvent which does not adversely influence the reaction (e.g. ethanol, etc.) under cooling to under heating in a conventional manner.

The object compounds of the above processes and preparations can be purified and converted to the desired salts in a conventional manner.

The object compound (I) of this invention and pharmaceutically acceptable salt thereof are thromboxane $A_2(TXA_2)$ antagonists and therefore useful as therapeutical agents for diseases caused by $TXA_2$ (e.g. thrombosis, asthma, etc.)

For illustration purpose, some biological data of the object compound (I) are shown in the followings.

In the following tests, the used 9, 11-azo $PGH_2$ and 9,11-methanoepoxy $PGH_2$(U46619) are characterized pharmacologically as $TXA_2$ mimetic agents and widely used for evaluating $TXA_2$ antagonism of test compounds (for example, vida The Journal of Pharmacology and Experimental Therapeutics Vol. 234, pp 435–441).

| Test compounds | |
|---|---|
| Test compounds No. | Formula |
| 1 | ![structure with O, CH₃, COOH, NNHCNH, S] |
| 2 | ![structure with O, CH₃, COOH, NNHCNH, O] |

Test 1 (Effect on 9,11-azo $PGH_2$ induced aggregation of rabbit platelet in vitro)

(a) TEST METHOD

In the in vitro experiments, the blood was collected from the carotid artery of rabbits into plastic vessels containing 0.1 volume of 3.8% aqueous sodium citrate. Platelet rich plasma (PRP) was prepared by centrifugation at 150 g for 15 minutes. Platelet aggregation was investigated using the turbidometric method with an aggregometer (NKK HEMATRACER 1). To the 225 μl of PRP, 25 μl of test compound solution was added, and then stirred at 1000 rpm for 2 minutes at 37° C. To the solution, 5 μl of 9,11-azo $PGH_2$ (final 1.0 μM) was added as an aggregating inducer. $IC_{50}$ (Inhibition concentration of platelet aggregation by 50%) were graphically determined.

(b) TEST RESULT

| Test compound No. | $IC_{50}$ (M) |
|---|---|
| 1 | $5.5 \times 10^{-8}$ |
| 2 | $2.6 \times 10^{-7}$ |

Test 2. (Effect on 9,11-methanoepoxy $PGH_2$ induced platelet aggregation ex vivo)

(a) TEST METHOD

In the ex vivo experiments, male Hartley strain guinea-pigs weighing about 300 g were used after overnight fasting Animals received an oral administration of test compound or vehicle 1 hour before the blood collection from abdominal artery. PRP was prepared as described above, and platelet aggregation was induced by adding 5 μl of 9,11-methanoepoxy $PGH_2$(U46619, 0.5 μM) to 250 μl of PRP.

(b) TEST RESULT

| Test compound No. | Dose (mg/kg) | Aggregation (%) | Inhibition (%) |
|---|---|---|---|
| Control | — | 76.4 ± 1.2 | 0 |
| 1 | 10 | 0.0 ± 0.0 | 100 |

The object compound (I) or its pharmaceutically acceptable salt can usually be administered to mammals including human being in the form of a conventional pharmaceutical composition such as capsule, microcapsule, tablet, granule, powder, troche, syrup, aerosol, inhalation, solution, injection, suspension, emulsion, suppository, ointment, or the like.

The pharmaceutical composition of this invention can contain various organic or inorganic carrier materials, which are conventionally used for pharmaceutical purpose, such as excipient (e.g. sucrose, starch, mannit, sorbit, lactose, glucose, cellulose, talc, calcium phosphate, calcium carbonate, etc.), binding agent (cellulose, methyl cellulose, hydroxypropylcellulose, polypropylpyrrolidone, gelatin, gum arabic, polyethyleneglycol, sucrose, starch, etc.), disintegrator (e.g. starch, carboxymethyl cellulose, calcium salt of carboxymethyl cellulose, hydroxypropylstarch, sodium glycole-starch, sodium bicarbonate, calcium phosphate, calcium citrate, etc.), lubricant (e.g. magnesium stearate, talc, sodium laurylsulfate, etc.), flavoring agent (e.g. citric acid, mentol, glycine, orange powders, etc.) preservative (sodium benzoate, sodium bisulfite, methylparaben, propylparaben, etc.), stabilizer (citric acid, sodium citrate, acetic acid, etc.), suspending agent e.g. methyl cellulose, polyvinylpyrrolidone, aluminum stearate, etc.), dispersing agent, aqueous diluting agent (e.g. water), base wax (e.g. cacao butter, polyethyleneglycol, white petrolatum, etc.).

A dosage of the present active ingredient is to be varied depending on various factors such as weight and/or age of a patient and/or the kind of the diseases, and further the kind of administration route. In general, an effective dosage can be selected from a range of about 1–50 mg/day for an oral route, about 0.1–5 mg/day for an intramuscular or intravenous injection.

The total daily amount mentioned above may be divisionally given to the patient at the interval of 6–12 hours per day. Preferable single dose of the present active ingredient may be, for example, about 100–500 mg per tablet or capsule, about 1.25–250 mg per vial or ampoule, and so on.

The following Examples are given for the purpose of illustrating this invention.

EXAMPLE 1

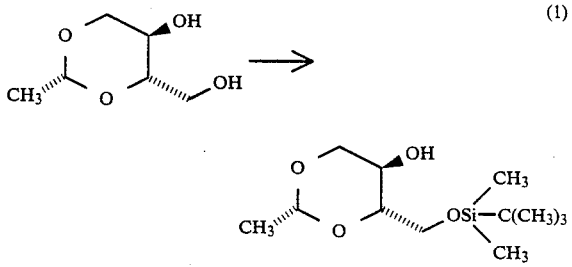

A mixture of (2R,4S,5R)-5-hydroxy-4-hydroxymethyl-2-methyl-1,3-dioxane (13.0 g), t-butyldimethylchlorosilane (14.5 g) and imidazol (13.1 g) in N,N-dimethylformamide (130 ml) was stirred at room temperature for 2 hours and the mixture was diluted with ethyl acetate (500 ml). The solution was washed successively with water, diluted hydrochloric acid, saturated aqueous sodium hydrogen carbonate and brine and dried over magnesium sulfate. The solvent was evaporated in vacuo to give (2R,4S,5R)-4-t-butyldimethylsiloxymethyl-5-hydroxy-2-methyl-1,3-dioxane (24.2 g) as a colorless oil.

$^1$H NMR (CDCl$_3$) δppm : 0.10 (3H, s), 0.12 (3H, s), 0.91 (9H, s), 1.32 (3H, d, J=5 Hz), 3.3–3.6 (3H, m), 3.7–3.8 (2H, m), 3.94 (1H, dd, J=4, 9 Hz), 4.13 (1H, dd, J=5, 9 Hz), 4.70 (1H, q, J=5 Hz)

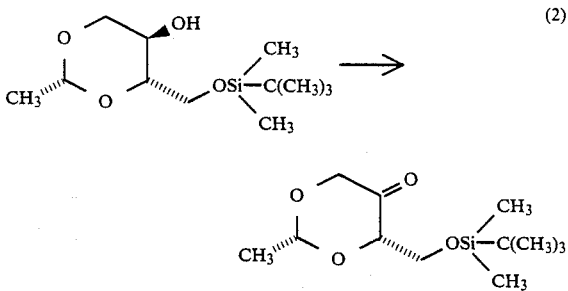

A solution of (2R,4S,5R)-4-t-butyldimethylsiloxymethyl-5-hydroxy-2-methyl-1,3-dioxane (4.2 g) in a mixture of benzene (30 ml) and dimethylsulfoxide (5.7 ml) were added pyridine (1.30 ml), trifluoroacetic acid (0.62 ml) and N,N'-dicyclohexylcarbodiimide (9.90 g) under cooling in an ice bath and the mixture was stirred at room temperature for 3 hours. The resulting solution were added ethyl acetate (50 ml) and water (30 ml) and stirred for 30 minutes. After removal of insoluble urea by filtration, the organic layer was separated and washed successively with water and brine. The solution was dried over magnesium sulfate and the solvent was evaporated in vacuo to give crude oil. The oil was purified with silica gel column (50 g) (n-hexane : ethyl acetate=10:1) to give (2R,4S) 4-t-butyldimethylsiloxymethyl-2-methyl-1,3-dioxan-5-one (3.22 g) as a pale yellow oil.

$^1$H NMR (CDCl$_3$) δppm : 0.07 (3H, s), 0.09 (3H, s), 0.89 (9H, s), 1.47 (3H, d, J=5.5 Hz), 3.98 (2H, d, J=3.5 Hz), 4.3–4.5 (3H, m), 5.11 (1H, q, J=5.5 Hz)

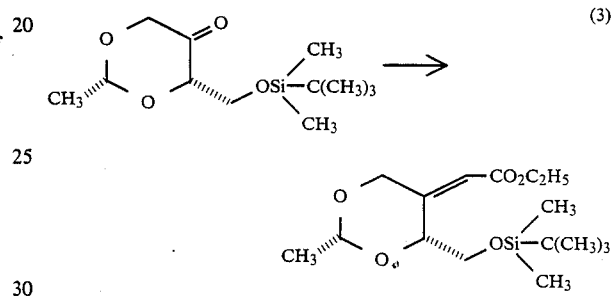

A mixture of (2R,4S)-4-t-butyldimethylsiloxymethyl-2-methyl-1,3-dioxan-5-one (2.50 g) and carboethoxymethylenetriphenylphosphorane (4.00 g) in tetrahydrofuran (25 ml) was stirred at room temperature for 24 hours and the solvent was evaporated in vacuo. The residue was chromatographed on a silica gel column (50 g) with a mixture of n-hexane and ethyl acetate (10:1) as an eluent to give (2R,4R)-4-t-butyldimethylsiloxymethyl-5-ethoxycarbonylmethylene-2-methyl-1,3-dioxane (2.09 g) as an oil.

$^1$H NMR (CDCl$_3$) δppm : 0.08 (6H, 2s), 0.90 (9H, s), 1.38 (3H, t, J=7.5 Hz), 1.47 (1H, d, J=5.0 Hz), 3.83 (1H, dd, J=9, 11 Hz), 3.87 (1H, dd, J=9, 11 Hz), 4.17 (1H, q, J=7.5 Hz), 4.30 (1H, m), 4.56 (1H, dd, J=17, 2 Hz), 4.93 (1H, q, J=5 Hz), 5.44 (1H, d, J=17 Hz), 5.89 (1H, m)

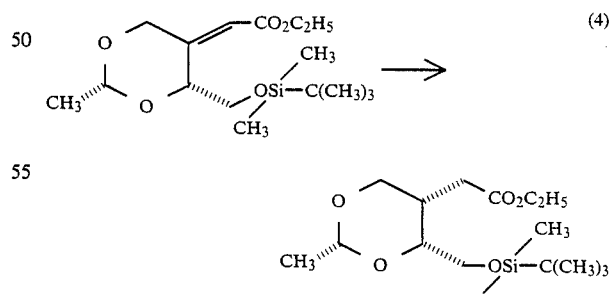

A solution of (2R,4R)-4-t-butyldimethylsiloxymethyl-5-ethoxycarbonylmethylene-2-methyl-1,3-dioxane (17.0 g) in ethanol (170 ml) was shaken under hydrogen (3 atm) with 10% palladium on carbon at room temperature for 1.5 hours. After removal of the catalyst by filtration, the solvent was evaporated in vacuo and the residue was chromatographed on a silica gel column (500 g) with a mixture of n-hexane and ethyl acetate (20:1) as an eluent to give (2R,4R,5S)-4-t-butyldimethylsiloxymethyl-5 -ethoxycarbonylmethyl-2-methyl-1,3-dioxane (9.52 g) as a pale yellow oil.

$^1$H NMR (CDCl$_3$) δppm : 0.07 (6H, 2s), 0.89 (9H, s), 1.26 (3H, t, J=7 Hz), 1.31 (3H, d, J=5 Hz), 2 06 (1H, m), 2.43 (1H, m), 2.71 (1H, dd, J=10, 16 Hz), 3.52 (1H, dd, J=7,11 Hz), 3.68 (1H,dd, J=7,11 Hz), 3.83 (1H, dt, J=2,11 Hz), 3.89 (1H, dt, J=3, 7 Hz), 4.06 (1H, d, J=12 Hz), 4.14 (2H, q, J=7 Hz), 4.72 (1H, q, J=5 Hz)

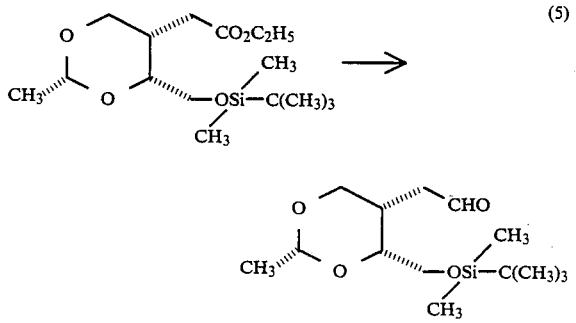

(5)

A solution of (2R,4R,5S)-4-t-butyldimethylsiloxymethyl-5-ethoxycarbonylmethyl-2-methyl-1,3-dioxane (9.30 g) in toluene (93 ml) was cooled in a dry ice acetone bath and to the solution was added dropwise diisobutyl aluminum hydride (1.5 M solution in toluene, 26.4 ml). The mixture was stirred at the same temperature for 1 hour. After quenching the mixture with saturated aqueous ammonium chloride, to the solution was added a mixture of ethyl acetate (300 ml) and water (300 ml). Insoluble materials were filtered off. The filtrate was extracted with ethyl acetate and organic layer was washed with brine and dried over magnesium sulfate. The solvent was evaporated in vacuo and the residue was chromatographed on a silica gel column (250 g) with a mixture of n-hexane and ethyl acetate (10:1) as an eluent to give (2R,4R,5S)-4-t-butyldimethylsiloxymethyl-5-formylmethyl -2-methyl-1,3-dioxane (6.61 g) as a colorless oil.

$^1$H NMR (CDCl$_3$) δppm : 0.08 (6H, 2s), 0.88 (9H, s), 1.31 (3H, d, J=5.5 Hz), 2.19 (1H, m), 2.63 (1H, dd, J=5, 17 Hz), 2.88 (1H, dd, J=9, 17 Hz), 3.50 (1H, dd, J=10,11 Hz), 3.68 (1H, dd, J=7,11 Hz), 3.8–4 1 (3H, m), 4.74 (1H, q, J=5.5 Hz)

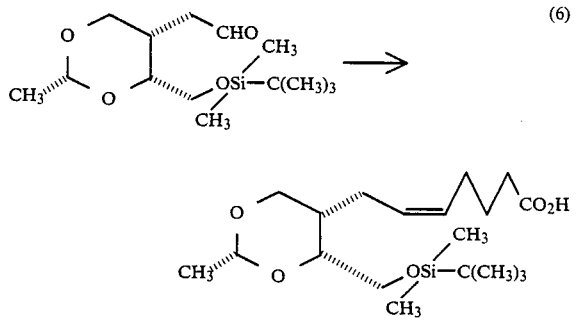

(6)

A suspension of sodium hydride (3.49 g, 60% in oil) in dimethylsulfoxide (75 ml) was heated at 75° C. for 1 hour and the resulting solution was cooled to room temperature. To the solution was added dropwise (4-carboxybutyl)triphenylphosphonium bromide (32.2 g) in dimethylsulfoxide (100 ml). After being stirred at room temperature for 15 minutes, to the mixture was added (2R,4R,5S)-4-t-butyldimethylsiloxymethyl-5-formylmethyl-2-methyl-1,3-dioxane (6.3 g) in dimethylsulfoxide (10 ml) and the solution was stirred at room temperature for 1.5 hour. To the reaction mixture was added aqueous ammonium chloride (100 ml) and the mixture was adjusted to pH 4 with oxalic acid. The mixture was extracted with ethyl acetate and the organic layer was washed successively with water and brine and dried over magnesium sulfate. The solvent was evaporated in vacuo and the residue was chromatographed on a silica gel column (150 g) with a mixture of n-hexane and ethyl acetate (10:1 - 1:1) as an eluent to give (2R,4R,5S)-4-t-butyldimethylsiloxymethyl-5-[(Z)-6-carboxy-2-hexenyl]-2-methyl-1,3-dioxane (5.50 g) as a colorless oil.

$^1$H NMR (CDCl$_3$) δppm : 0.07 (6H, 2s), 0.89 (9H, s), 1.31 (3H, d, J=5 Hz), 1.50 (1H, m), 1.6–1.8 (2H, m), 2.0–2.2 (3H, m), 2.3–2.6 (3H, m), 3.5–3.8 (3H, m), 3.89 (1H, m), 4.02 (1H,d, J=11 Hz), 4.73 (1H, q, J=5 Hz), 5.3–5.6 (2H, m)

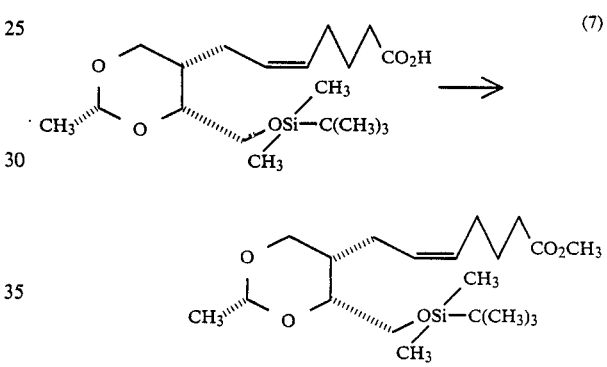

(7)

A solution of (2R,4R,5S)-4-t-butyldimethylsiloxymethyl-5-[(Z)-6-carboxy-2-hexenyl]-2-methyl-1,3-dioxane (4.75 g) in N,N-dimethylformamide (50 ml) were added potassium carbonate (1.76 g) and methyl iodide (1.62 ml) and the mixture was stirred at room temperature for 5 hours. The solution was poured into water and the resulting aqueous solution was extracted with ether. The organic layer was washed successively with water and brine and dried over magnesium sulfate. The solvent was evaporated in vacuo and the residue was chromatographed on a silica gel column (75 g) with a mixture of n-hexane and ethyl acetate (20:1) as an eluent to give (2R,4R,5S) -4-t-butyldimethylsiloxymethyl-5-[(Z)-6-methoxycarbonyl-2-hexenyl]-2-methyl-1,3-dioxane (4.17 g) as an oil.

$^1$H NMR (CDCl$_3$) δppm : 0.07 (6H, 2s), 0.96 (9H, s), 1 31 (3H, d, J=5.0 Hz), 1.48 (1H, m), 1.6–1.8 (2H, m), 2.0–2.2 (3H, m), 2.3–2.6 (3H, m), 3.5–3.7 (3H, m), 3.68 (3H, s), 3.89 (1H, m), 4.00 (1H, d, J=11 Hz), 4.72 (1H, q, J=5 Hz), 5.3–5.6 (2H, m)

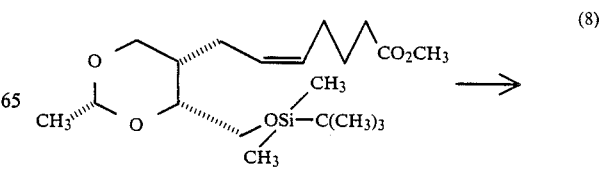

(8)

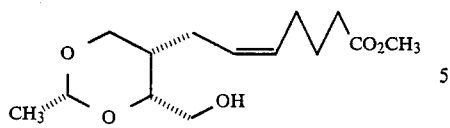

A mixture of (2R,4R,5S)-4-t-butyldimethylsiloxymethyl-5-[(Z)-6-methoxycarbonyl-2-hexenyl]-2-methyl-1,3-dioxane (4.00 g) and tetra-n-butyl ammonium fluoride (15 mmole) in tetrahydrofurane (40 ml) was stirred at room temperature for 3 hours and the solvent was evaporated in vacuo. The residue was chromatographed on a silica gel column (80 g) with a mixture of n-hexane and ethyl acetate (20:15) as an eluent to give (2R,4R,5S) -4-hydroxy-methyl-5-[(Z)-6-methoxycarbonyl-2-hexenyl]-2-methyl-1,3-dioxane (2.88 g) as colorless oil.

$^1$H NMR (CDCl$_3$) ppm : 1.35 (3H, d, J=5.0 Hz), 1.43 (1H, m), 1.6–1.8 (2H, m), 1.9–2.2 (3H, m), 2.3–2.6 (3H, m), 3.68 (3H, s), 3.7–3.9 (3H, m), 3.93 (1H, m), 4.00(1H, dd, J=2, 12.5 Hz), 4.76 (1H, q, J=5.0 Hz), 5.3–5.6 (2H, m)

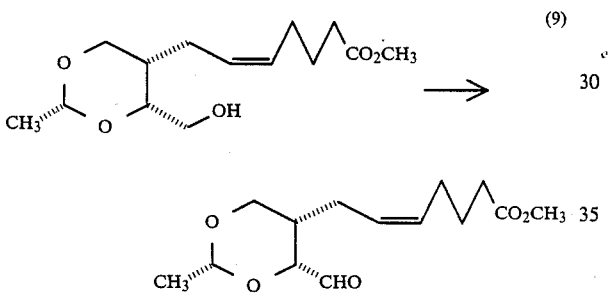

To a solution of pyridine (1.64 ml) in dichloromethane (45 ml) was added chromium trioxide (1.07 g) at 10° C. and the solution was stirred at room temperature for 1 hour. The solution was cooled in an ice bath and was added (2R,4R,5S)-4-hydroxymethyl-5-[(Z)-6-methoxycarbonyl-2-hexenyl]-2-methyl-1,3-dioxane (500 mg) in dichloromethane (3 ml). After being stirred at room temperature for 2 hours, the solution was diluted with ether (100 ml) and passed through a silica gel column. The eluate was evaporated in vacuo and the residue was chromatographed on a silica gel column (20 g) with a mixture of n-hexane and ethyl acetate (1:1) as an eluent to give (2R,4R,5S)-4-formyl-5-[(Z)-6-methoxycarbonyl-2-hexenyl]-2-methyl-1,3-dioxane (336 mg) as a colorless oil.

$^1$H NMR (CDCl$_3$) δppm : 1.43 (3H, d, J=5.5 Hz), 1.5–1.8 (3H, m), 1.91 (1H, m), 2.0–2.2 (2H, m), 2.3–2.4 (2H, m), 2.55 (1H, m), 3.69 (3H, s), 3.78 (1H, m), 4.03 (1H, dd, J=2,11 Hz), 4.27 (1H, d, J=2 Hz), 4.80 (1H, q, J=5.5 Hz), 5.3–5.6 (2H, m), 9.62 (1H, s)

To a mixture of 2R,4R, 5S)-4-formyl-5-[(Z)-6-methoxycarbonyl-2-hexenyl]-2-methyl-1,3-dioxane (62 mg) and 4-phenyl-3-thiosemicarbazide (46 mg) in ethanol (2 ml) was added acetic acid (1 drop) and the solution was stirred at room temperature for 4 hours. The mixture was diluted with chloroform (15 ml) and the solution was washed with brine and dried over magnesium sulfate. The solvent was evaporated in vacuo to give (2R,4R,5S)-5-[(Z)-6-methoxycarbonyl-2-hexenyl]-2-methyl-4-[4-(phenyl)thiosemicarbazonomethyl]-1,3-dioxane (110 mg) as an oil.

$^1$H NMR (CDCl$_3$) δppm : 1.38 (3H, d, J=5 Hz), 1.5–1.8 (3H, m), 2.0–2.2 (3H, m), 2.2–2.4 (2H, m), 2.53 (1H, m), 3.69 (3H, s), 3.85 (1H, m), 4.05 (1H, m), 4.53 (1H, dd, J=3, 4.5 Hz), 4.82 (1H, m), 5.3–5.6 (2H, m), 7.2–7.5 (4H, m), 7.62 (3H, m), 9.04 (1H, s), 9.73 (1H, s)

A solution of (2R,4R,5S)-5-[(Z)-6-methoxycarbonyl-2-hexenyl[-2-methyl-4-[4-(phenyl)thiosemicarbazonomethyl]-1,3-dioxane (110 mg) in a mixture of methanol (2 ml) and 1N sodium hydroxide (1 ml) was stirred at room temperature for 2 hours and the mixture was adjusted to pH 7 with 1N hydrochloric acid. The solvent was evaporated in vacuo and the residue was dissolved in a mixture of chloroform and methanol (3:1, 10 ml). The solution was dried over magnesium sulfate and the solvent was evaporated in vacuo to give a crude oil. The oil was purified with preparative TLC to give (2R,4R,5S)-5-[(Z)-6-carboxy-2-hexenyl]-2-methyl-4-[4-(phenyl)thiosemicarbazonomethyl]-1,3-dioxane (65 mg) as an oil.

$^1$H NMR (CDCl$_3$) δppm : 1.42 (3H, d, J=5 Hz), 3.88 (1H, dd, J=11.5, 2 Hz), 4.10 (1H, d, J=11.5 Hz), 4.56 (1H, dd, J=2.3, 5.2 Hz), 4.83 (1H, q, J=5 Hz), 5.55 (2H, m), 7.2–7.7 (6H, m), 9.07 (1H, s), 10.8 (1H, br s)

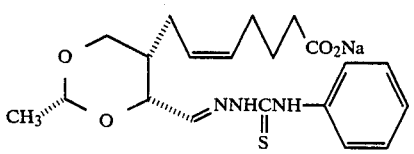

A solution of (2R,4R,5S)-5-[(Z)-6-carboxy-2-hexanyl]-2-methyl-4-[4-(phenyl)thiosemicarbazonomethyl]-1,3-dioxane (1.39 g) in a mixture of methanol (10 ml) and 1N aqueous sodium hydroxide (3.43 ml) was stirred at room temperature for 2 hours and the solvent was evaporated in vacuo. The residue was dissolved in water (50 ml) and the solution was subjected to a column of Diaion HP-20 (trademark, sold by Mitsubishi Chemical Industries Ltd.) (200 ml). The column was washed with water (500 ml) and the object compound was eluted with a mixture of water and methanol (1:1, 1 l). The solvent was concentrated in vacuo and the residue was liophilized to give (2R,4R,5S)-5-[(Z)-6-carboxy-2-hexenyl]-2-methyl-4-[4-(phenyl)thiosemicarbazonomethyl]-1,3-dioxane sodium salt (1.77 g) as a pale yellow powder.

$^1$H NMR (D$_2$O) δppm : 1.39 (3H, d, J=5.5 Hz), 1.5-1.7 (3H, m), 1.9-2.1 (3H, m), 2.1-2.3 (4H, m), 2.37 (1H, m), 4.05 (1H, s), 4.98 (1H, q, J=5.5 Hz), 4.8-5.1 (2H, m), 7.3-7.5 (6H, m)

EXAMPLE 2

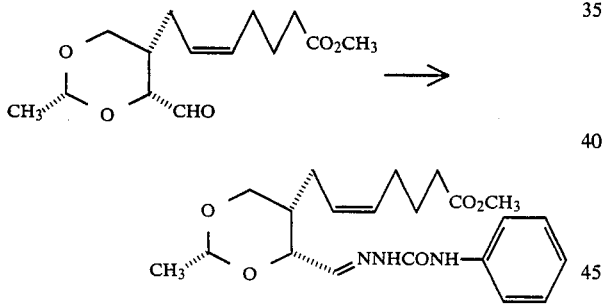

A mixture of (2R,4R,5S)-4-formyl-5-[(Z)-6-methoxycarbonyl-2-hexenyl]-2-methyl-1,3-dioxane (300 mg), 4-phenylsemicarbazide (227 mg) and a few drops of acetic acid in methanol (5 ml) was stirred at room temperature for 3 hours and the mixture was diluted with chloroform (30 ml). The solution was washed with brine and dried over magnesium sulfate. The solvent was evaporated in vacuo and the residue was chromatographed on a silica gel column (15 g) with a mixture of n-hexane and ethyl acetate (3:1) as an eluent to give (2R,4R,5S)-5-[(Z)-6-methoxycarbonyl-2-hexenyl]-2-methyl-4-(4-phenylsemicarbazonomethyl)-1,3-dioxane (403 mg) as an pale yellow oil.

$^1$H NMR (CDCl$_3$) δppm : 1.40 (3H, d, J=5.5 Hz), 1.6-1.8 (3H, m), 2.0-2.2 (3H,m), 2.2-2.4 (2H, m), 2.55 (1H, m), 3.69 (3H, s), 3.85 (1H, m), 4.04 (1H, m), 4.57 (1H, dd, J=3, 4.5 Hz), 4.85 (1H, m), 5.3-5.6 (2H, m), 7.09 (1H, t, J=7 Hz), 7.18 (1H, d, J=5 Hz), 7.35 (2H, m), 7.50 (3H, m), 7.95 (1H, s), 8.53 (1H, s)

EXAMPLE 3

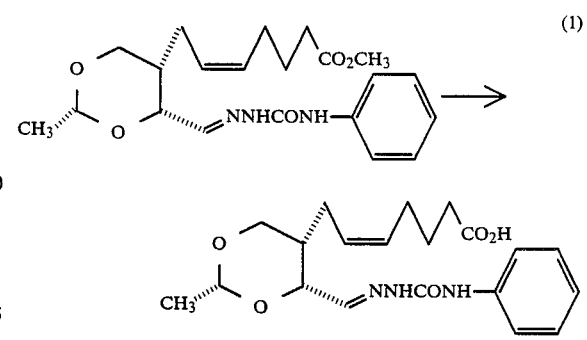

A solution of (2R,4R,5S)-5-[(Z)-6-methoxycarbonyl-2-hexenyl]-2-methyl-4-(4-phenylsemicarbazonomethyl) -1,3-dioxane (403 mg) in a mixture of methanol (9 ml) and 1N aqueous sodium hydroxide (5 ml) was stirred at room temperature for 4 hours and the mixture was adjusted to pH 7 with 1N-hydrochloric acid. The solvent was evaporated in vacuo and the residue was dissolved in a mixture of chloroform and methanol (3:1, 30 ml). The solution was dried over magnesium sulfate and the solvent was concentrated in vacuo to give crude oil. The crude product was chromatographed on a silica gel column (15 g) with a mixture of n-hexane, ethyl acetate and acetic acid (25:75:1) as an eluent to give (2R,4R,5S) -5-[(Z)-6-carboxy-2-hexanyl]-2-methyl-4 -(4-phenylsemicarbazonomethyl)-1,3-dioxane (203 mg) as an pale yellow oil.

$^1$H NMR (CDCl$_3$) δppm : 1.39 (3H, d, J=5.5 Hz), 1.5-1.8 (3H, m), 2.0-2.2 (2H, m), 2.3-2.6 (3H, m), 3.87 (1H,dd, J=2, 13 Hz), 4.09 (1H, d, J=13 Hz), 4.55 (1H, dd, J=2, 5 Hz), 4.83 (1H, q, J=5.5 Hz), 5.4-5.6 (2H, m), 7.10 (1H, t, J=7.5 Hz), 7.2-&.4 (4H,m), 7.50 (2H, m), 8.05 (1H,s), 9.40 (1H,s)

(2) The following salt was prepared in a similar manner to that of Example 1(12).

(2R,4R,5S)-5-[(Z)-6-Carboxy-2-hexanyl]-2-methyl-4-(4-phenylsemicarbonomethyl)-1,3-dioxane sodium salt.

$^1$H NMR (D$_2$O) δppm: 1.41 (3H, d, J=5.5 Hz), 1.5-1.7 (3H, m) 1.8-2.4 (8H, m), 4.02 (1H, s), 4.95 (1H, q, J=5.5 Hz), 5.3-5.6 (2H, m), 7.21 (1H, m), 7.4-7.5 (5H, m)

EXAMPLE 4

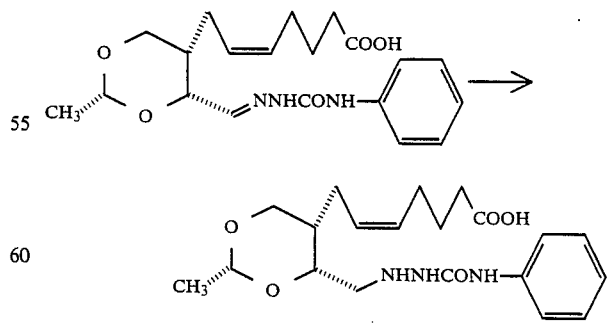

To a solution of (2R,4R,5S)-5-[(Z)-6-carboxy-2-hexanyl]-2-methyl-4-(4-phenylsemicarbazono)methyl-1,3-dioxane (48 mg) in ethanol (2 ml) was added sodium cyanoborohydride (15 mg) and acetic acid (1 drop) and the mixture was stirred at room temperature for 2 hours.

The solvent was evaporated in vacuo and the residue was extracted with chloroform at pH 3 and the organic layers were combined and dried over anhydrous sodium sulfate. The solvent was evaporated in vacuo and the crude product was purified with preparative TLC with ethyl acetate to give (2R,4R,5S)-5-[(Z)-6-carboxy-2-hexenyl]-2-methyl-4 -(4-phenylsemicarbazido methyl)-1,3-dioxane (22 mg).

$^1$H NMR (CDCl$_3$) δppm : 1.32 (3H, d, J=5 Hz), 1.6–1.9 (2H, m), 2.0–2.2 (4H, m), 2.36 (2H, t, J=7 Hz), 2.4–2.6 (1H, m), 2.85 (1H, dd, J=2.6, 12.8 Hz), 3.05 (1H, dd, J=9.7, 12.8 Hz), 3.72 (1h, m), 4.01 (1H, m), 4.70 (1H, q, J=5 Hz), 5.4–5.6 (2H, m), 7.04 (1H, t, 7.3 Hz), 7.30 (2H, m), 7.45 (2H, d, J=7.5 Hz), 8.28 (1H, s)

EXAMPLE 5

The following compound was prepared in a similar manner to that of Example 2.

(2R,4R,5S)-4-t-Butoxycarbonylhydrazonomethyl-5-[(Z)-6-methoxycarbonyl-2 -hexenyl]-2-methyl-1,3-dioxane $^1$H NMR (CDCl$_3$) δppm : 1.35 (3H, d, J=5 Hz), 1.50 (9H, s), 1.6–1.8 (3H, m), 2.0–2.2 (2H, m), 2.2–2.4 (2H, m), 2.50 (1H, m), 3.68 (3H, s), 3.78 (1H, d, J=11.5 Hz), 3.98 (1H, d, J=11.5 Hz), 4.58 (1H, dd, J=2, 5 Hz), 4.77 (1H, q, J=5 Hz), 5.3–5.6 (2H, m), 7.23 (1H, m), 8.01 (1H, s)

EXAMPLE 6

The following compound was prepared in a similar manner to that of Example 3.

(2R,4R,5S)-4-t-Butoxycarbonylhydrazonomethyl-5-[(Z)-6-carboxy-2-hexanyl]-2-methyl-1,3-dioxane $^1$H NMR (CDCl$_3$) δppm : 1.2–1.5 (1H, m), 1.35 (3H, d, J=5 Hz); 1.50 (9H, s), 1.6–1.8 (3H, m), 2.0–2.2 (2H, m), 2.35 (2H, d, J=6.5 Hz), 2.46 (1H, m), 3.77 (1H, m), 4.04 (1H, d, J=11 Hz), 4.57 (1H, m), 4.80 (1H, m), 5.3–5.5 (2H, m), 7.21 (1H, m), 7.26 (1H, s)

EXAMPLE 7

The following compound was prepared in a similar manner to that of Example 2.

(2R,4R,5S)-5-[(Z)-6-Methoxycarbonyl-2-hexenyl]-2-methyl-4-(1-phthalazinylhydrazonomethyl)-1,3-dioxane $^1$H NMR (CDCl$_3$) δppm : 1.33 (3H, d, J=5.5 Hz), 1.6–1.8 (3H, m), 2.0–2.2 (2H, m), 2.43 (2H, t, J=8 Hz), 2.67 (1H, m), 3.67 (1H, m), 3.85 (1H, d, J=12 Hz), 4.05 (1H, d, J=12 Hz), 4.68 (1H, dd, J=3, 4 Hz), 4.87 (1H, q, J=5.5 Hz), 5.3–5.6 (2H, m), 7.51 (1H, m), 7.6–7.7 (2H, m), 7.88 (1H, m), 7.36 (1H, m), 10.48 (1H, broad)

EXAMPLE 8

The following compound was prepared in a similar manner to that of Example 3.

(2R,4R,5S)-5-[(Z)-6-Carboxy-2-hexenyl]-2-methyl-4 -(1-phthalazinylhydrazonomethyl)-1,3-dioxane $^1$H NMR (CDCl$_3$) δppm : 1.45 (3H, d, J=5.5 Hz), 1.6–1.9 (3H, m), 2.0–2.2 (3H, m), 2.3–2.6 (3H, m), 3.90 (1H, dd, J=2,11 Hz), 4.18 (1H, d, J=11 Hz), 4.70 (1H, dd, J=3, 4 Hz), 4.88 (1H, q, J=5.5 Hz), 5.4–5.7 (2H, m), 7.56 (1H, m), 7.6–7.8 (2H, m), 7.90 (1H, m), 7.98 (1H, m), 8.41 (1H, m)

EXAMPLE 9

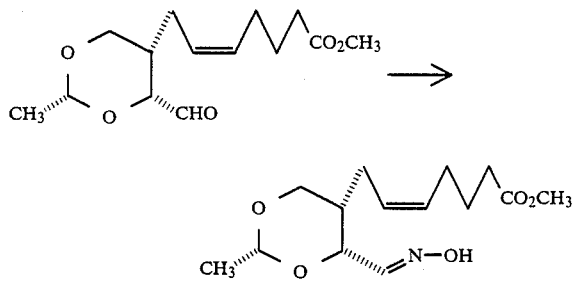

A mixture of (2R,4R,5S)-4-formyl-5-[(Z)-6-methoxycarbonyl-2-hexenyl]-2-methyl-1,3-dioxane (326 mg), hydroxylamine hydrochloride (374 mg) and sodium hydrogen carbonate (374 mg) in a mixture of methanol (6 ml) and water (3 ml) was stirred at room temperature for 3 hours. To the solution were added chloroform and brine and organic layer was separated. The organic layer was dried over magnesium sulfate and evaporated in vacuo. The residue was chromatographed on a silica gel column (15 g) with a mixture of n-hexane and ethyl acetate (5:1) as an eluent.

(2R,4R,5S)-(Z)-4-Hydroxyiminomethyl-5-[(Z)-6-methoxycarbonyl-2-hexenyl]-2-methyl-1,3-dioxane (100 mg) was obtained from the first fractions.

$^1$H NMR (CDCl$_3$) δppm : 1.35 (1H, d, J=5 Hz), 1.6–1.8 (3H, m), 1.9–2.2 (4H, m), 2.34 (2H, d, J=7.5 Hz), 2.57 (1H, m), 3.69 (3H, s), 3.81 (1H, d, J=11.5 Hz), 3.98 (1H, d, J=11.5 Hz), 4.79 (1H, q, J=5 Hz), 4.98 (1H, dd, J=3.5, 4.5 Hz), 5.4–5.6 (2H, m), 6.78 (d, J=3.5 Hz), 8.00 (1H, s)

(2R,4R,5S)-(E)-4-Hydroxyiminomethyl-5-[(Z)-6 -methoxycarbonyl-2-hexenyl]-2-methyl-1,3-dioxane (142 mg) was obtained from the second fractions.

$^1$H NMR (CDCl$_3$) δppm : 1.37 (3H, d, J=5 Hz), 1.58 (1H, m), 1.6–1.8 (2H, m), 2.0–2.2 (2H, m), 2.27 (1H, m), 2.85 (2H, t, J=7.5 Hz), 2.55 (1H, m), 3.69 (3H, s), 3.80 (1H, d, J=11.5 Hz), 4.03 (1H, d, J=11.5 Hz), 4.55 (1H, dd, J=2, 4.5 Hz), 4.80 (1H, q, J=5 Hz), 5.3–5.6 (2H, m), 7.43 (1H, d, J=4.5 Hz), 7.83 (1H, s)

EXAMPLE 10

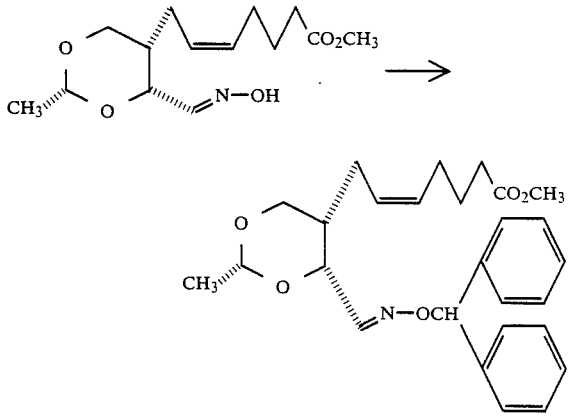

To a solution of (2R,4R,5S)-(E)-4-hydroxyiminomethyl-5-[(Z)-6-methoxycarbonyl-2-hexenyl]-2-methyl-1,3-dioxane (100 mg) in N,N-dimethylformamide (5 ml) was added sodium hydride (14 mg 60% in oil) at 5° C. After being stirred at the same temperature for 30 minutes, to the solution was added diphenylmethyl bromide (86.6 mg) and the mixture was stirred in an ice bath for additional 2 hours. The solution was diluted with ethyl acetate and washed successively with water and brine, dried over magnesium sulfate. The solvent was evaporated in vacuo and the crude residue was purified with preparative TLC with a mixture of n-hexane and ethyl acetate (4:1) as an eluent to give (2R,4R,5S)-(E)-4-diphenylmethoxyiminomethyl-5-[(Z)-6-methoxycarbonyl-2-hexenyl]-2-methyl-1,3-dioxane $^1$H NMR (CDCl$_3$) δppm : 1.34 (3H, d, J=5 Hz), 1.49 (1H, m), 1.6–1.8 (3H, m), 2.0–2.2 (3H, m), 2.32 (2H, t, J=7.5 Hz), 2.55 (1H, m), 3.68 (3H, s), 3.70 (1H, d, J=11.5 Hz), 3.96 (1H, d, J=11.5 Hz), 4.49 (1H, dd, J=2, 5.5 Hz), 4.74 (1H, q, J=5 Hz), 5.2–5.5 (2H, m), 6.23 (1H, s), 7.2–7.4 (11H, m), 7.59 (1H, d, J=5.5 Hz)

EXAMPLE 11

The following compound was prepared in a similar manner to that of Example 3.

(2R,4R,5S)-5-[(Z)-6-Carboxy-2-hexenyl]-4-diphenylmethoxyiminomethyl-2-methyl-1,3-dioxane $^1$H NMR (CDCl$_3$) δppm : 1.34 (3H, d, J=5 Hz), 1.50 (1H, m), 1.6–1.8 (3H, m), 2.0–2.2 (3H, m), 2.85 (2H, t, J=7.5 Hz), 2.59 (1H, m), 3.77 (1H, m), 3.96(1H,d,J=11.5 Hz), 4.50 (dd, J=2.5, 5.5 Hz), 4.74 (1H, m), 5.00(1H, dd, J=2.5, 4.5 Hz), 5.2–5.6 (2H, m), 6.22 (1H, s), 6.78(1H,d,J=4.5 Hz), 7.2–7.4 (1H, m), 7.56(1H,d,J=5.5 Hz)

EXAMPLE 12

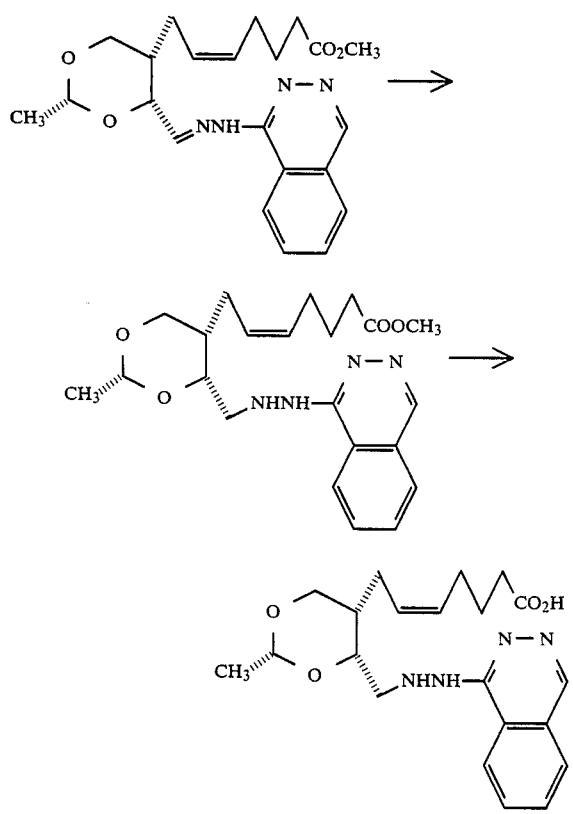

To a solution of (2R,4R,5S)-5-[(Z)-6-methoxycarbonyl-2-hexenyl]-2-methyl-4-(1-phthalazinylhydrazonomethyl)-1,3-dioxane (450 mg) in a mixture of methanol (4 ml) and acetic acid (2 ml) was added sodium cyanoborohydride (125 mg) and the mixture was stirred at room temperature for 2 hours. The solution was adjusted to pH 7 with saturated aqueous sodium hydrogen carbonate and the resulting mixture was diluted with chloroform. The solution was washed successively with water and brine and dried over magnesium sulfate. The solvent was evaporated in vacuo to give (2R,4R,5S)-5-[(Z)-6-methoxycarbonyl-2-hexenyl]-2-methyl-4-(1-phthalazinylhydrazinomethyl)-1,3-dioxane as a residue and the residue was dissolved in a mixture of methanol (5 ml) and 1N aqueous sodium hydroxide (2 ml). After being stirred at room temperature overnight, the mixture was neutralized with 1N hydrochloric acid and the resulting solution was evaporated to dryness in vacuo. The residue was purified with preparative thin layer chromatography with a mixture of chloroform and methanol (10:1) as in eluent to give (2R,4R,5S)-5-[(Z)-6-carboxy-2-hexenyl]-2-methyl-4-(1-phthalazinylhydrazinomethyl)-1,3-dioxane (96.3 mg) as a pale yellow oil.

$^1$H NMR (CDCl$_3$) δppm : 1.44 (1H, d, J=5 Hz), 1.5–1.9 (3H, m), 1.9–2.2 (3H, m), 2.3–2.6 (3H, m), 3.88 (1H, d, J=12.5 Hz), 4.15 (1H, d, J=12.5 Hz), 4.70 (1H, m), 4.87 (1H, q, J=5 Hz), 5.4–5.7 (2H, m), 7.57 (1H, m), 7.6–7.8 (2H, m), 7.9–8.1 (2H, m), 8.41 (1H, m), 9.60 (1H, s)

EXAMPLE 13

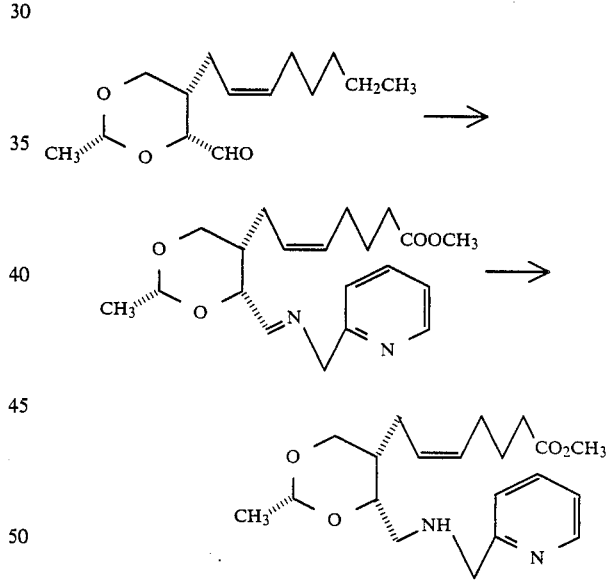

To a mixture of (2R,4R,5S)-4-formyl-5-[(Z)-6-methoxycarbonyl-2-hexenyl]-2-methyl-1,3-dioxane (200 mg) and 2-aminomethylpyridine (0.15 ml) in a mixture of methanol (4 ml) and acetic acid (1 ml) was added sodium cyanoborohydride (100 ml) and the solution was stirred at room temperature overnight. The mixture was neutralized with saturated aqueous sodium hydrogen carbonate and extracted with chloroform. The organic extract was washed with brine and dried over magnesium sulfate. The solvent was evaporated in vacuo and the residue was chromatographed on a silica gel column (10 g) with a mixture of chloroform and methanol (30:1) as an eluent to give (2R,4R,5S)-5-[(Z)-6-methoxycarbonyl-2-hexenyl]-2-methyl-4-(2-pyridylmethylaminomethyl)-1,3-dioxane (165 mg).

¹H NMR (CDCl₃) δppm : 1.33 (3H, d, J=5 Hz), 1.40 (1H, m), 1.6–1.8 (2H, m), 1.9–2.0 (2H, m), 2.0–2.2 (3H, m), 2.32 (2H, d, J=7.5 Hz), 2.48 (1H, m), 2.63 (1H, dd, J=3.5, 12.5 Hz), 2.90 (1H, dd, J=3.5, 12.5 Hz), 3.66 (3H, s), 3.70 (1H, m), 3.95 (2H, m), 4.01 (1H, m), 4.74 (1H, q, J=5 Hz), 5.3–5.6 (2H, m), 7.07 (1H, dd, J=5, 7.5 Hz), 7.32 (1H, d, J=7.5 Hz), 7.66 (1H, dt, J=1.5, 10 Hz), 8.56 (1H, d, J=5 Hz)

EXAMPLE 14

The following compound was prepared in a similar manner to that of Example 3.

(2R,4R,5S)-5-[(Z)-6-carboxy-2-hexenyl]-2-methyl-4-(2-pyridylmethylaminomethyl)-1,3-dioxane ¹H NMR (CDCl₃) δppm : 1.27 (1H, m), 1.30 (1H, d, J=5 Hz), 1.45 (1H, m), 1.5–1.8 (2H, m), 2.05 (1H, m), 2.2–2.4 (4H, m), 2.8–3.0 (2H, m), 3.72 (1H, dd, J=1.5, 11.5 Hz), 3.9–4.2 (4H, m), 4.73 (1H, q, J=5 Hz), 5.3–5.6 (2H, m), 5.94 (1H, broad), 7.2–7.4 (2H, m), 7.72 (1H, dt, J=1.5, 10 Hz), 8.65 (1H, d, J=5 Hz)

EXAMPLE 15

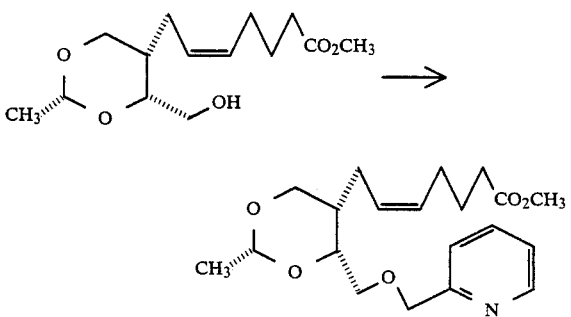

To a solution of (2R,4R,5S)-4-hydroxymethyl-5-[(Z)-6-methoxycarbonyl-2-hexenyl]-2-methyl-1,3-dioxane (272 mg) in N,N-dimethylformamide (10 ml) were added sodium hydride (80 mg, 60% in oil) and 2-picolyl chloride hydrochloride (110 mg) and the mixture was stirred at room temperature overnight. The reaction mixture was quenched with saturated aqueous ammonium chloride and the resulting solution was extracted with ethyl acetate. The organic layer was washed with brine and dried over magnesium sulfate. The solvent was evaporated in vacuo and the residue was purified with preparative thin layer chromatography with ethyl acetate as an eluent to give (2R,4R,5S)-5-[(Z)-6-methoxycarbonyl-2-hexenyl]-2-methyl-4-(2-pyridylmethoxymethyl)-1,3-dioxane (201 mg) as a pale yellow oil.

¹H NMR (CDCl₃) δppm : 1.35 (3H, d, J=5.5 Hz), 1.47 (1H, m), 1.6–1.8 (3H, m), 1.9–2.2 (3H, m), 2.2–2.4 (2H, m), 2.50 (1H, m), 3.57 (1H, dd, J=5, 10 Hz), 3.67 (3H, s), 3.74 (1H, m), 4.00 (1H, d, J=12 Hz), 4.13 (1H, m), 4.70 (2H, ABq, J=13 Hz), 4.78 (1H, q, J=5.5 Hz), 5.3–5.6 (2H, m), 7.19 (1H, dd, J=5, 7 Hz), 7.45 (1H, d, J=8 Hz), 7.71 (1H, dt, J=1.5, 8 Hz), 8.55 (1H, d, J=5 Hz)

EXAMPLE 16

The following compound was prepared in a similar manner to that of Example 3.

(2R,4R,5S)-5-[(Z)-6-Carboxy-2-hexenyl]-2-methyl-4-(2-pyridylmethoxymethyl)-1,3-dioxane ¹H NMR (CDCl₃) δppm : 1.33 (3H, d, J=5 Hz), 1.49 (1H, m), 1.6–1.9 (3H, m), 2.0–2.3 (4H, m), 2.38 (2H, t, J=7 Hz), 3.6–3.8 (2H, m), 4.0–4.1 (2H, m), 4.70 (2H, ABq, J=13 Hz), 4.77 (1H, q, J=5 Hz), 5.4–5.6 (2H, m), 7.33 (1H, dd, J=5, 7 Hz), 7.48 (1H, d, J=8 Hz), 7.80 (1H, dt, J=1.5, 8 Hz), 8.69 (1H, d, J=5 Hz)

EXAMPLE 17

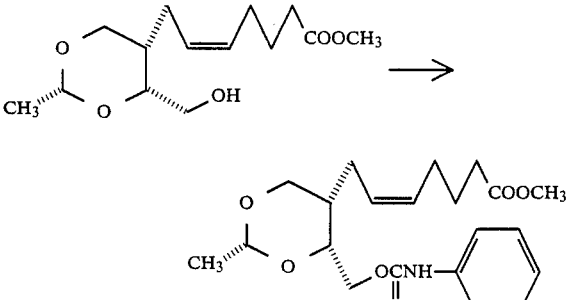

To a solution of (2R,4R,5S)-4-hydroxymethyl-5-[(Z)-6-methoxycarbonyl-2-hexenyl]-2-methyl-1,3-dioxane (108 mg) in pyridine (0.5 ml) was added phenyl isocyanate (0.1 ml) and the mixture was stirred at room temperature for 30 minutes. Water (1 ml) was added and extracted with ether and the organic layers were combined and dried over anhydrous sodium sulfate. The solvent was evaporated in vacuo and the crude product was purified with preparative TLC (hexane:ether=1:1) to give (2R,4R,5S)-5-[(Z)-6-methoxycarbonyl-2-hexenyl]-2-methyl-4-phenylcarbamoyloxymethyl-1,3-dioxane (140 mg).

¹H NMR (CDCl₃) δppm : 1.36 (3H, d, J=5 Hz), 1.4–1.8 (3H, m), 2.0–2.3 (3H, m), 2.33 (2H, t, J=7 Hz), 2.4–2.6 (1H, m), 3.67 (3H, s), 3.72 (1H, m), 3.95–4.25 (4H, m), 4.75 (1H, q, J=5 Hz), 5.3–5.6 (2H, m), 6.94 (1H, br s), 7.07 (1H, m), 7.3–7.5 (4H, m)

EXAMPLE 18

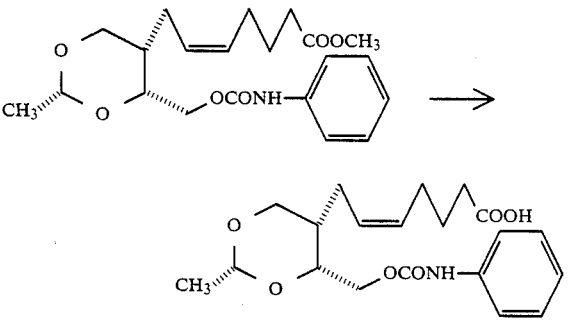

To a solution of (2R,4R,5S)-5-[(Z)-6-methoxycarbonyl-2-hexenyl]-2-methyl-4-phenylcarbamoyloxymethyl-1,3-dioxane (140 mg) in methanol (2 ml) was added 1 ml of 1N aqueous sodium hydroxide and stirred at room temperature for 90 minutes. The reaction mixture was evaporated in vacuo and the residue was neutralized by acetic acid and extracted with ethyl acetate. The organic layers were combined and dried over anhydrous sodium sulfate. The solvent was evaporated to dryness and the crude product was purified with preparative TLC (ether : dichloromethane=1:1) to give (2R,4R,5S)-5-[(Z)-6-carboxy-2-hexenyl]-2-methyl-4-phenylcarbamoyloxymethyl-1,3-dioxane (115 mg).

¹H NMR (CDCl₃) δppm : 1.35 (3H, d, J=5 Hz), 1.4–1.8 (3H, m), 2.0–2.3 (3H, m), 2.38 (2H, t, J=7 Hz), 2.4–2.6 (1H, m), 3.73 (1H, m), 4.0–4.4 (4H, m), 4.75 (1H, q, J=5 Hz), 5.3–5.6 (2H, m), 6.88 (1H, br s), 7.0–7.15 (1H, m), 7.3–7.5 (4H, m)

EXAMPLE 19

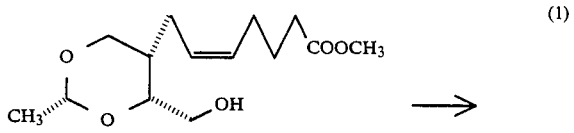

To a solution of (2R,4R,5S)-4-hydroxymethyl-5-[(Z)-6-methoxycarbonyl-2-hexenyl]-2-methyl-1,3-dioxane (456 mg) in pyridine (2 ml) was added p-toluenesulfonyl chloride (640 mg) and the mixture was stirred at room temperature for 2 hours. Water (10 ml) was added to the mixture and extracted with ethyl acetate and the organic layers were washed with aqueous sodium bicarbonate (5 ml) and brine (5 ml), and the crude product was dried over sodium sulfate. The solvent was evaporated in vacuo and the crude product was dissolved in dimethylsulfoxide (2 ml) and added potassium phthalimide (550 mg) and the mixture was stirred at 100° C. for 6 hours. The reaction mixture was cooled and added to water, and extracted with ether. The organic layers were combined and dried over anhydrous sodium sulfate. The solvent was evaporated in vacuo and the crude product was purified with preparative TLC to give (2R,4R,5S)-5-[(Z)-6-methoxycarbonyl-2-hexenyl]-2-methyl-4-phthalimidomethyl-1,3-dioxane (400 mg).

$^1$H NMR (CDCl$_3$) δppm : 1.28 (3H, d, J=5 Hz), 1.3–1.9 (4H, m), 2.0–2.5 (5H, m), 2.63 (1H, m), 3.69 (3H, s), 3.6–3.8 (2H, m), 4.00 (2H, m), 4.18 (1H, m), 4.63 (1H, q, J=5 Hz), 5.3–5.6 (2H, m), 7.7–7.9 (4H, m)

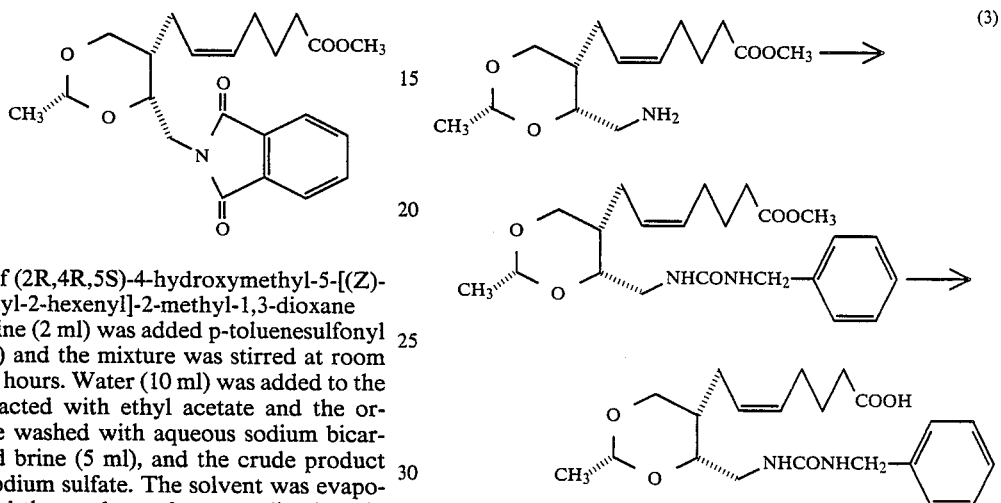

To a solution of (2R,4R,5S)-5-[(Z)-6-methoxycarbonyl-2-hexenyl]-2-methyl-4-phthalimidomethyl-1,3-dioxane (54 mg) in ethanol (2 ml) was added hydrazine monohydrate (0.007 ml) and the mixture was stirred at room temperature overnight. The solvent was evaporated in vacuo and the crude product was purified with preparative TLC (chloroform:methanol:conc.aqueous ammonia=85:15:0.1) to give (2R,4R,5S)-4-aminomethyl-5-[(Z)-6-methoxycarbonyl-2-hexenyl]-2-methyl-1,3-dioxane (13 mg).

$^1$H NMR (CDCl$_3$) δppm : 1.33 (3H, d, J=5 Hz), 1.69 (2H, m), 1.9–2.2 (3H, m), 2.32 (2H, t, J=7.6 Hz), 2.3–2.6 (2H, m), 2.71 (1H, m), 2.94 (1H, dd, J=9, 13 Hz), 3.68 (3H, s), 3.65–3.85 (2H, m), 3.98 (1H, d, J=11.2 Hz), 4.73 (1H, q, J=5 Hz), 5.3–5.6 (2H, m)

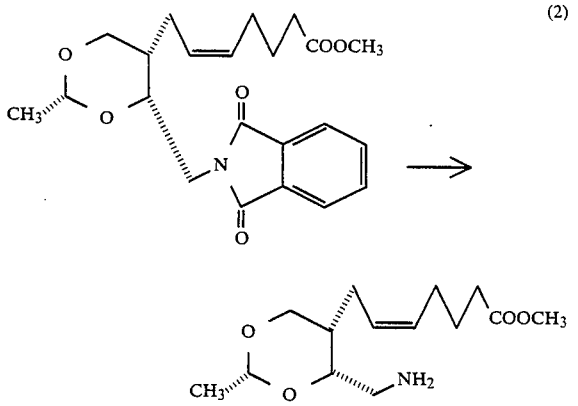

To a solution of (2R,4R,5S)-4-aminomethyl-5-[(Z)-6-methoxycarbonyl-2-hexenyl]-2-methyl-1,3-dioxane (13 mg) in pyridine (0.3 ml) was added benzyl isocyanate (0.02 ml) and the mixture was stirred at room temperature for 60 minutes. Water (0.1 ml) was added and the solvent was evaporated in vacuo to give (2R,4R,5S)-4-(3-benzylureidomethyl)-5-[(Z)-6-methoxycarbonyl-2-hexenyl]-2-methyl-1,3-dioxane as a residue. The residue was dissolved in methanol (1.5 ml) and added 0.3 ml of 1N aqueous sodium hydroxide and stirred at room temperature for 4 hours. The reaction mixture was evaporated in vacuo and the residue was neutralized with 1N hydrochloric acid and extracted with ethyl acetate. The organic layers were combined and dried over anhydrous sodium sulfate. The solvent was evaporated to dryness and the crude product was purified with preparative TLC (ethyl acetate as an eluent) to give (2R,4R,5S)-4-(3-benzylureidomethyl)-5-[(Z)-6-carboxy-2-hexenyl]-2-methyl-1,3-dioxane (20 mg).

$^1$H NMR (CDCl$_3$) δppm : 1.22 (3H, d, J=5 Hz), 1.68 (2H, m), 1.9–2.3 (3H, m), 2.32 (2H, t, J=6.5 Hz), 3.18 (1H, m), 3.38 (1H, m), 3.6–4.1 (3H, m), 4.2–4.4 (2H, m), 4.63 (1H, q, J=5 Hz), 5.3–5.7 (3H, m), 7.1–7.4 (5H, m)

EXAMPLE 20

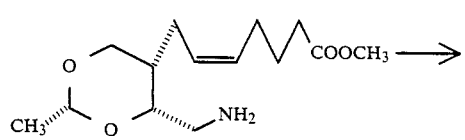

-continued

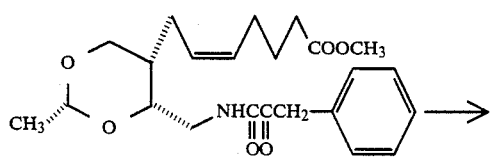

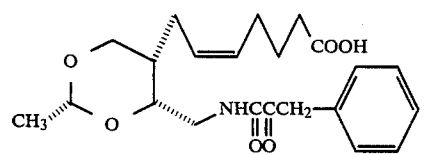

To a solution of (2R,4R,5S)-4-aminomethyl-5-[(Z)-6-methoxycarbonyl-2-hexenyl]-2-methyl-1,3-dioxane (35 mg) in ethyl acetate (2.4 ml) was added N,N'-dicyclohexylcarbodiimide (33.6 mg) and benzylglyoxylic acid (27 mg) and the mixture was stirred at room temperature overnight. The reaction mixture was filtered and the filtrate was evaporated in vacuo to give (2R,4R,5S)-4-benzylglyoxyloylaminomethyl-5-[(Z)-6-methoxycarbonyl-2-hexenyl]-2-methyl-1,3-dioxane as a residue. The residue was dissolved in methanol (1.5 ml) and added 0.5 ml of 1N aqueous sodium hydroxide and stirred at room temperature for 2 hours. The reaction mixture was evaporated in vacuo and the residue was neutralized with 1N hydrochloric acid and extracted with ethyl acetate. The organic layers were combined and dried over anhydrous sodium sulfate. The solvent was evaporated to dryness and the crude product was purified with preparative TLC (chloroform:ethyl acetate=1:1) to give (2R,4R,5S)-4-benzylglyoxyloylaminomethyl-5-[(Z)-6-carboxy-2-hexenyl]-2-methyl-1,3-dioxane (12 mg).

$^1$H NMR (CDCl$_3$) δppm : 1.30 (3H, d, J=5 Hz), 1.5–1.8 (2H, m), 2.0–2.2 (2H, m), 2.36 (2H, t, J=7 Hz), 2.47 (1H, m), 3.21 (1H, m), 3.5–4.0 (4H, m), 4.22 (2H, s), 4.67 (1H, q, J=5 Hz), 5.3–5.6 (2H, m), 7.1–7.4 (5H, m)

EXAMPLE 21

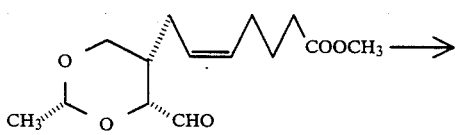

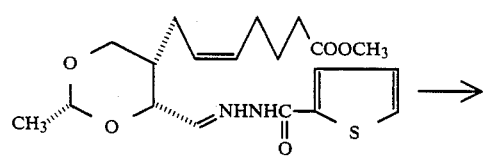

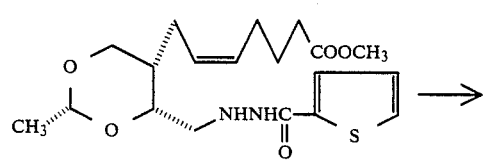

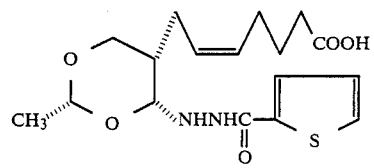

To a solution of (2R,4R,5S)-4-formyl-5-[(Z)-6-methoxycarbonyl-2-hexenyl]-2-methyl-1,3-dioxane (47 mg) in ethanol (1 ml) was added thenohydrazide (27 mg) and the mixture was stirred at room temperature for 1 hour, and then added sodium cyanoborohydride (20 mg) and acetic acid (0.25 ml) and the mixture was stirred for 1 hour. Aqueous sodium bicarbonate was added and extracted with chloroform and the organic layers were combined and dried over anhydrous sodium sulfate. The solvent was evaporated in vacuo to give (2R,4R,5S)-5-[(Z)-6-methoxycarbonyl-2-hexenyl]-2-methyl-4-(N'-thenoylhydrazino)methyl-1,3-dioxane as a residue and the residue was dissolved in methanol (2 ml) and added 1N aqueous sodium hydroxide (0.4 ml) and stirred at room temperature for 4 hours. The reaction mixture was evaporated in vacuo and the residue was neutralized with 1N hydrochloric acid and extracted with chloroform. The organic layers were combined and dried over sodium sulfate. The solvent was evaporated in vacuo and the crude product was purified with preparative TLC (ethyl acetate as an eluent) to give (2R,4R,5S)-5-[(Z)-6-carboxy-2-hexenyl]-2-methyl-4-(N'-thenoylhydrazino)methyl-1,3-dioxane (55 mg).

$^1$H NMR (CDCl$_3$) δppm : 1.34 (3H, d, J=5 Hz), 1.5–1.9 (2H, m), 2.0–2.5 (4H, m), 2.36 (2H, t, J=7 Hz), 3.03 (1H, dd, J=3.8, 12.5 Hz), 3.18 (1H, dd, J=8.1, 12.5 Hz), 3.74 (2H, m), 4.04 (3H, m), 4.75 (1H, q, J=5 Hz), 5.3–5.6 (2H, m), 7.10 (1H, m), 7.55 (2H, m)

EXAMPLE 22

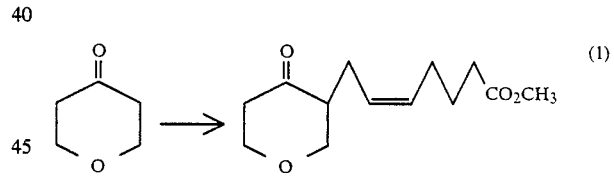

(1)

To a solution of lithium diisopropylamide (2.40 mmol) in tetrahydrofuran (5 ml), prepared from diisopropylamine (0.35 ml) with n-butyllithium (1.7 ml, 1.5 M solution in hexane) using an usual manner, was added 4-oxotetrahydropyran (220 mg) in tetrahydrofuran (2 ml) at −78° C. and the mixture was stirred for 30 minutes at the same temperature. To the resulting solution was added methyl(Z)-7-bromo-5-heptenate (500 mg) in tetrahydrofuran (2 ml) at −78° C. After being stirred at room temperature for 5 hours, the reaction mixture was quenched with saturated aqueous ammonium chloride and the solution was extracted with ethyl acetate. The organic layer was washed successively with water and brine and dried over magnesium sulfate. The solvent was evaporated in vacuo and the residue was chromatographed on a silica gel column (10 g) with a mixture of n-hexane and ethyl acetate (4:1) as an eluent to give 3-[(Z)-6-methoxycarbonyl-2-hexenyl]-4-oxo-tetrahydropyran (100 mg) as a colorless oil.

$^1$H NMR (CDCl$_3$) δppm : 1.6–1.8 (2H, m), 2.0–2.2 (2H, m), 2.34 (2H, t, J=8 Hz), 2.4–2.7 (4H, m), 3.42 (1H, dd, J=9, 11 Hz), 3.77 (1H, dt, J=4, 11 Hz), 3.98 (1H, m), 4.1–4.3 (2H, m), 5.25–5.35 (2H, m)

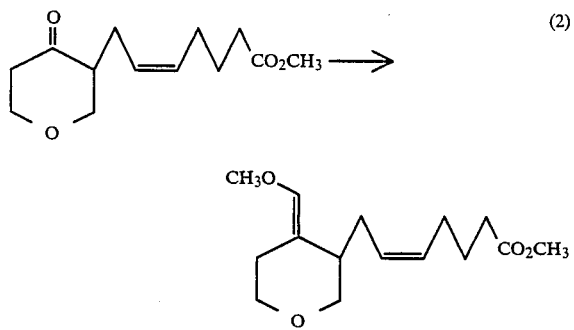

To a solution of (methoxymethyl)triphenylphosphonium chloride (3.17 g) in dimethylsulfoxide (20 ml) was added dimsyl sodium prepared from sodium hydride (370 mg, 60% in oil) with dimethylsulfoxide (25 ml) at room temperature. After being stirred at room temperature for 30 minutes, to the resulting mixture was added 3-[(Z)-6-methoxycarbonyl-2-hexenyl]-4-oxotetrahydropyran (740 mg) in dimethylsulfoxide (2 ml) and the solution was stirred at room temperature for additional 4 hours. The reaction mixture was poured into a mixture of water (100 ml) and ethyl acetate (100 ml) and the organic layer was separated, washed successively with water and brine and dried over magnesium sulfate. The solvent was evaporated in vacuo and the residue was chromatographed on a silica gel column (30 g) with a mixture of n-hexane and ethyl acetate (4:1) as an eluent to give 3-[(Z)-6-methoxycarbonyl-2-hexenyl]-4-methoxymethylenetetrahydropyran (279 mg) as a colorless oil.

$^1$H NMR (CDCl$_3$) δppm : 1.6–1.8 (3H, m), 1.9–2.2 (3H, m), 2.2–2.4 (4H, m), 3.2–3.7 (3H, m), 3.55 (3H, s), 3.67 (3H, s), 3.7–3.9 (2H, m), 5.3–5.5 (2H, m), 5.84 (1H, s)

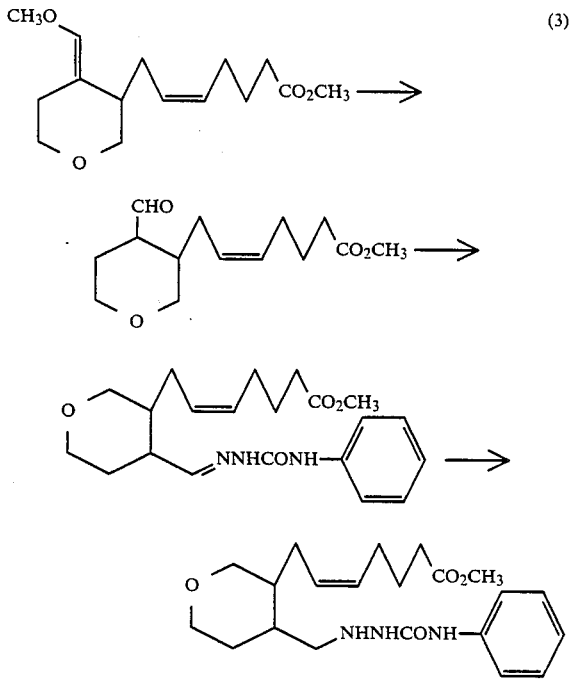

A solution of 3-[(Z)-6-methoxycarbonyl-2-hexenyl]-4-methoxymethylenetetrahydropyran in a mixture of methanol (10 ml) and 50% aqueous trifluoroacetic acid (10 ml) was stirred at room temperature for 1 hour and the solvent was evaporated in vacuo to give 4-formyl-3-[(Z)-6-methoxycarbonyl-2-hexenyl]tetrahydropyran as a residue. The residue was dissolved in methanol (10 ml). To the solution were added 4-phenylsemicarbazide (200 mg) and sodium cyanoborohydride (100 ml) and the mixture was stirred at room temperature for 2 hours. The mixture was diluted with chloroform (50 ml) and the solution was washed successively with saturated aqueous sodium hydrogen carbonate and brine. The solution was dried over magnesium sulfate and the solvent was evaporated in vacuo. The residue was chromatographed on a silica gel column (10 g) with a mixture of n-hexane and ethyl acetate (3:1) as an eluent to give 3-[(Z)-6-methoxycarbonyl-2-hexenyl]-4-(4-phenylsemicarbazidomethyl)tetrahydropyran (266 mg) as a pale yellow oil.

$^1$H NMR (CDCl$_3$) δppm : 1.4–1.7 (5H, m), 1.9–2.2 (4H, m), 2.2–2.4 (3H, m), 2.7–3.0 (2H, m), 3.3–3.5 (2H, m), 3.69 (3H, s), 3.7–4.1 (2H, m), 5.2–5.5 (2H, m), 5.97 (1H, s), 7.04 (1H, t, J=7 Hz), 7.28 (3H, m), 7.34 (1H, s), 7.45 (2H, m), 8.10 (1H, s)

(4) The following compound was prepared in a similar manner to that of Example 3.

3-[(Z)-6-carboxy-2-hexenyl]-4-(4-phenylsemicarbazidomethyl)tetrahydropyran $^1$H NMR (CDCl$_3$) δppm : 1.5–1.8 (4H, m), 2.0–2.2 (4H, m), 2.36 (2H, t, J=7 Hz), 2.80 (1H, m), 2.96 (1H, m), 3.09 (1H, m), 3.3–3.6 (2H, m), 3.77 (1H, m), 3.9–4.0 (2H, m), 5.4–5.6 (2H, m), 7 05 (1H, t, J=8 Hz), 7.2–7.4 (3H, m), 7.33 (1H, s), 7.4–7.5 (2H, m), 8.15 (1H, s)

EXAMPLE 23

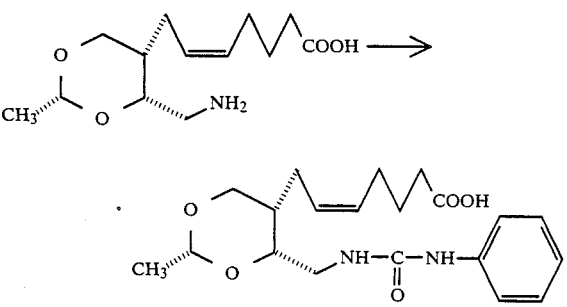

To a solution of (2R,4R,5S)-4-aminomethyl-5-[(Z)-6-carboxy-2-hexenyl]-2-methyl-1,3-dioxane (50 mg) in pyridine (0.5 ml) was added phenylisocyanate (0.1 ml) and stirred at room temperature for 1 hour. To this mixture water (1 ml) was added and stirred for 2 hours. The reaction mixture was diluted with ethyl acetate and the organic layer was washed with 1N hydrochloric acid. The organic layer was evaporated in vacuo and the crude residue was purified with preparative TLC to give (2R,4R,5S)-5-[(Z)-6-carboxy-2-hexenyl]-2-methyl-4-(3-phenylureidomethyl)-1,3-dioxane (27 mg).

$^1$H NMR (CDCl$_3$) δppm : 1.32 (3H, d, J=5 Hz), 1.45 (1H, m), 1.5–1.8 (2H, m), 2.0–2.4 (4H, m) 2.37 (2H, t, J=6.5 Hz), 3.2–3.5 (2H, m) 3.68 (1H, dd, J=11.3, 2 Hz), 3.94 (1H, m), 4.03 (4.03 (1H, d, J=11.3 Hz), 4.71 (1H, q, J=5 Hz), 5.4–5.6 (2H, m), 5.74 (1H, br t, J=6 Hz), 7.02 (1H, m) 7.1–7.4 (4H, m), 7.55 (1H, br s)

EXAMPLE 24

The following compound was prepared in a similar manner to that of Example 3.

(2R,4r, 5S)-5-[(Z)-6-carboxy-2-hexanyl]-2-methyl -4- (2-pyridylhydrazonomethyl)-1,3-dioxane.

$^1$H NMR (CDCl$_3$) δppm : 1.41 (3H, d, J=5 Hz), 1.53 (1H, m), 1.6–1.9 (2H,m) 2.0–2.2 (2H, m), 2.35–2.55 (4H, m), 3.85 (1H, dd, J=11.3, 2.5 Hz), 4.08 (1H, d, J=11.3 Hz), 4.55 (1H, dd, J=5, 3 Hz), 4.83 (1H, q, J=5 Hz), 5.4–5.6 (2H, m), 6.76 (1H, br t, J=6 Hz), 7.25 (1H, d, J=9 Hz), 7.40 (1H, d, J=5.5 Hz), 7.62 (1H, m) 7.93 (1H, br d, J=5.5 Hz)

We claim:

1. A compound of the formula:

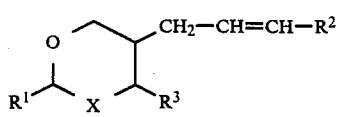

wherein

R$^1$ is hydrogen or lower alkyl,

R$^2$ is carboxy(lower)alkyl or protected carboxy(lower)alkyl and

R$^3$ is —CH=N—R$^4$ in which R$^4$ is arylureido or arylthioureido and

X is —O—, or pharmaceutically acceptable salt thereof.

2. The compound of claim 1, in which R$^2$ is carboxy)lower)alkyl or lower alkoxycarbonyl(lower)alkyl.

3. The compound of claim 2, in which R$^4$ is phenylureido or phenylthioureido.

4. The compound of claim 3, in which R$^1$ is hydrogen or methyl, and R$^2$ is carboxypropyl or methoxycarbonylpropyl 5. The compound of claim 1, in which R$^1$ is lower alkyl, and R$^2$ is carboxy(lower)alkyl 6. The compound of claim 5, which is (2R,4R,5S)-5-[(z)-6- carboxy-2-hexenyl]-2-methyl-4-(4-phenylsemicarbazonomethyl)-1,3-dioxane or pharmaceutically acceptable salt thereof.

7. The compound of claim 5, which is 2R,4R,5S)-5-[(z)-6-carboxy-2-hexanyl]-2-methyl-4-[4-(phenyl)thiosemicarbazonomethyl]-1,3-dioxane or pharmaceutically acceptable salt thereof.

8. A thromboxane A$_2$-antagonist pharmaceutical composition comprising an effective amount of a compound of the formula:

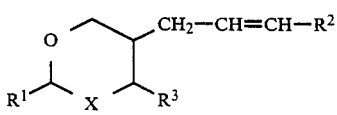

wherein

R$^1$ is hydrogen or lower alkyl,

R$^2$ is carboxy(lower)alkyl or protected carboxy(lower)alkyl and

R$^3$ is —CH=N—R$^4$ in which R$^4$ is arylureido or arylthioureido and

X is —O—, or pharmaceutically acceptable salt thereof and pharmaceutically acceptable carrier.

9. A method for treatment of diseases caused by thromboxane A$_2$ which comprises administering to a human or animal an effective amount of a compound

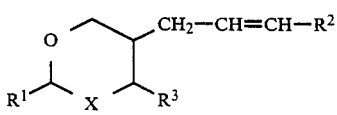

wherein

R$^1$ is hydrogen or lower alkyl,

R$^2$ is carboxy(lower)alkyl or protected carboxy(lower)alkyl and

R$^3$ is —CH=N—R$^4$ in which R$^4$ is arylureido or arylthioureido and

X is —O—, or pharmaceutically acceptable salt thereof.

* * * * *